United States Patent [19]

Louis

[11] Patent Number: 5,641,750

[45] Date of Patent: Jun. 24, 1997

[54] METHODS FOR TREATING PHOTORECEPTORS USING GLIAL CELL LINE-DERIVED NEUROTROPHIC FACTOR (GDNF) PROTEIN PRODUCT

[75] Inventor: Jean-Claude Louis, Thousand Oaks, Calif.

[73] Assignee: Amgen Inc., Thousand Oaks, Calif.

[21] Appl. No.: 564,833

[22] Filed: Nov. 29, 1995

[51] Int. Cl.$^6$ .............................. A61F 2/00; A61K 47/00; A61K 31/685
[52] U.S. Cl. ........................... 514/12; 435/69.1; 435/69.4
[58] Field of Search .............................. 514/12; 435/69.1, 435/69.4

[56] References Cited

U.S. PATENT DOCUMENTS

| | | | |
|---|---|---|---|
| 3,981,303 | 9/1976 | Higuchi et al. | 128/260 |
| 3,986,510 | 10/1976 | Higuchi et al. | 128/260 |
| 3,995,635 | 12/1976 | Higuchi et al. | 128/260 |
| 4,188,373 | 2/1980 | Krezanosk | 128/260 |
| 4,217,898 | 8/1980 | Theeuwes | 424/78 |
| 4,474,452 | 10/1984 | Haslam | 424/78 |
| 4,474,751 | 10/1984 | Haslam et al. | 424/78 |
| 4,474,752 | 10/1984 | Haslam et al. | 424/78 |
| 4,518,584 | 5/1985 | Mark et al. | 424/85.1 |
| 4,853,224 | 8/1989 | Wong | 424/427 |
| 4,863,457 | 9/1989 | Lee | 424/428 |
| 4,865,846 | 9/1989 | Kaufman | 424/428 |
| 4,882,150 | 11/1989 | Kaufman | 424/428 |
| 4,892,538 | 1/1990 | Aebischer et al. | 664/891.1 |
| 5,011,472 | 4/1991 | Aebischer et al. | 604/892.1 |
| 5,106,627 | 4/1992 | Aebischer et al. | 530/399 |
| 5,221,696 | 6/1993 | Ke et al. | 514/786 |
| 5,252,714 | 10/1993 | Harris et al. | 530/391.9 |
| 5,384,333 | 1/1995 | Davis et al. | 724/405 |
| 5,422,116 | 6/1995 | Yen et al. | 424/427 |

FOREIGN PATENT DOCUMENTS

| | | |
|---|---|---|
| 154316 | 9/1985 | European Pat. Off. . |
| 401384 | 12/1990 | European Pat. Off. . |
| 423980 | 4/1991 | European Pat. Off. . |
| WO91/10425 | 7/1991 | WIPO . |
| WO91/10470 | 7/1991 | WIPO . |
| WO93/06116 | 4/1993 | WIPO . |
| WO93/15608 | 8/1993 | WIPO . |
| WO93/21902 | 11/1993 | WIPO . |

OTHER PUBLICATIONS

Malik et al., "T6F-B Superfamily Members Promote Survival of Midbrain Dopaminergil Neurons and Protect Them Against MPP+ Toxicity", EMBO Journal, vol. 14(4) pp. 736-742 (1995).

"Transplantation of Photoreceptors to Light-Damaged Retina", M. S. Silverman and S. E. Hughes, Investigative Orthalodoxy and Visual Science, vol. 3/8, Aug., pp. 1684-1690 (1989).

LaVail et al., "Multiple Growth Factors, Lytokines, and Neurotrophineresine Photoreceptors from the Damaging Effects of Constant Light", Proc. Natl. Acad. Sci., vol. 89, Dec., pp. 11249-11253 (1992).

Aebischer et al. (1991), 'Long-Term Cross-Species Brain Transplantation of a Polymer-Encapsulated Dopamine-Secreting Cell Line', Exper. Neurol. 111:269-275.

Batchelor et al. (1989), 'Nerve Growth Factor Receptor and Choline Acetyltransferase Colocalization in Neurons Within the Rat Forebrain: Response to Fimbria-Fornix Transection', J. Comp. Neurol. 284:187-204.

Beck et al. (1995), 'Mesencephalic dopaminergic neurons protected by GDNF from axotomy-induced degeneration in the adult brain', Nature 373:339-341.

Bothwell (1995), 'Functional Interactions of Neurotrophins and Neurotrophin Receptors', Ann. Rev. Neurosci. 18:223-253.

Chamow et al. (1994), 'Modification of CD4 Immunoadhesin with Monomethoxypoly (ethylene glycol) Aldehyde via Reductive Alkylation', Bioconjugate Chem. 5:133-140.

Chao et al. (1995), 'p75 and Trk: a two-receptor system', TINS 18:321-326.

Cunningham and Wells (1989), 'High-Resolution Epitope Mapping of hGH-Receptor Interactions by Alanine-Scanning Mutagenesis', Science 224:1081-1085.

Dayhoff (1972), Atlas of Protein Sequence and Structure 5:124.

Faktorovich et al. (1990), 'Photoreceptor degeneration in inherited retinal dystrophy delayed by basic fibroblast growth factor', Nature 347:83-86.

Francis (1992), 'Protein modification and fusion proteins', Focus on Growth Factors 3(2):4-10.

Gouras et al. (1990), 'Transplantation of retinal cells', Neuro-Ophthalmol. 10:165-176.

Gurny, R. et al. (1987), 'Design and Evaluation of Controlled Release Systems for the Eye', Journal of Controlled Release 6:367-373.

Hefti (1994), 'Neurotrophic Factor Therapy for Nervous System Degernative Diseases', J. Neurobiol. 25:1418-1435.

Henderson et al. (1994), 'GDNF: A Potent Survival Factor for Motoneurons Present in Peripheral Nerve and Muscle', Science 266:1062-1064.

(List continued on next page.)

Primary Examiner—Howard E. Schain
Assistant Examiner—P. Lynn Touzeau
Attorney, Agent, or Firm—Daniel R. Curry; Ron K. Levy; Steven M. Odre

[57] ABSTRACT

The present invention relates generally to methods for treating injury or degeneration of retinal neurons, and in particular photoreceptors, by administering glial cell line-derived neurotrophic factor (GDNF). The invention relates specifically to methods for treating retinal conditions or diseases in which vision is lost such as retinitis pigmentosa, age-related macular degeneration, diabetic retinopathy, peripheral vitreoretinopathies, photic retinopathies, surgery-induced retinopathies, viral retinopathies, ischemic retinopathies, retinal detachment and traumatic retinopathy.

19 Claims, 6 Drawing Sheets

OTHER PUBLICATIONS

Hoffer et al. (1994), 'Glial cell line–derived neurotrophic factor reverses toxin–induced injury to midbrain dopaminergic neurons in vivo', *Neurosci. Lett.* 182:107–111.

Hudson et al. (1995), 'Glial Cell Line–derived Neurotrophic Factor Augments Midbrain Dopaminergic Circuits In Vivo', *Brain Res. Bull.* 36:425–432.

Kastner et al. (1994), 'Glial cell–line derived neurotrophic factor (GDNF) mRNA upregulation in striatum and cortical areas after pilocarpine–induced status epilepticus in rats', *Mol. Brain Res.* 26:325–330.

Kiss et al. (1988), 'Immunohistochemical Localization of Cells Containing Nerve Growth Factor Receptors in the Different Regions of the Adult Rat Forebrain', *Neurosci.* 27:731–748.

Krieglstein et al. (1995), 'TGF–β superfamily members promote survival of midbrain dopaminergic neurons and protect them against MPP$^+$ toxicity', *EMBO J.* 14:736–742.

Lapchak et al. (1993), 'Neurotrophins in the Central Nervous System', *Rev. Neurosci.* 3:1–10.

LaVail et al. (1992), 'Multiple growth factors, cytokines, and neurotrophins rescue photoreceptors from the damaging effects of constant light', *Proc. Natl. Acad. Sci. USA* 89:11249–11253.

Li and Turner (1988), 'Inherited Retinal Dystrophy in the RCS Rat: Prevention of Photoreceptor Degeneration of Pigment Epithelial Cell Transplantation', *Exp. Eye Res.* 47:911–917.

Lin et al. (1993), 'GDNF: A Glial Cell Line–Derived Neurotrophic Factor for Midbrain Dopaminergic Neurons', *Science* 260:1130–1132.

Louis et al. (1992), 'Receptor–Mediated Toxicity of Norepinephrine on Cultured Catecholaminergic Neurons of the Rat Brain Stem[1]', *J. Pharmacol. Exp. Therap.* 262:1274–1283.

Louis et al. (1993), 'CNTF Protection of Oligodendrocytes Against Natural and Tumor Necrosis Factor–Induced Death', *Science* 259:689–692.

Malik et al. (1992), 'Polyethylene Glycol (PEG)–modified Granulocyte–Macrophage Colony–stimulating Factor (GM–CSF) with Conserved Biological Activity', *Exp. Hematol.* 20:1028–1035.

Miller et al. (1994), 'Central Adminstration of rhGDNF Causes Augmentation of Dopaminergic Activity In Vivo', *Soc. Neurosci. Abstr.* 20:1300.

Mullen and La Vail (1976), 'Inherited Retinal Dystrophy: Primary Defect in Pigment Epithelium Determined with Experimental Rat Chimeras', *Science* 192:799–801.

Olson, Lars (1994), 'Neurotrophins in Neurodegenerative Disease: Theoretical Issues and Clinical Trials', *Neurochem. Inc.* 25:1–3.

Oppenheim et al. (1995), 'Developing motor neurons rescued form programmed and axotomy–induced cell death by GDNF', *Nature* 373:344–346.

Poulsen et al. (1994), 'TGFβ2 and TGFβ3 Are Potent Survival Factors for Midbrain Dopaminergic Neurons', *Neuron* 13:1245–1252.

Schaar et al. (1994), 'Multiple Astrocyte Transcripts Encode Nigral Trophic Factors in Rat and Human', *Exp. Neurol.* 130:387–393.

Schaar et al. (1993), 'Regional and Cell–Specific Expression of GDNF in Rat Brain', *Exp. Neurol.* 124:368–371.

Silverman and Hughes (1989), 'Transplantation of Photoreceptors to Light–Damaged Retina', *Invest. Ophthalmol. Vis. Sci.* 30:1684–1690.

Spring et al. (1994), 'Brief Communication Expression of GDNF mRNA in Rat and Human Nervous Tissue', *Exp. Neurol.* 127:167–170.

Stromberg et al. (1993), 'Brief Communication Glial Cell Line–Derived Neurotrophic Factor is Expressed in the Developing but not Adult Striatum and Stimulates Developing Dopamine Neurons in Vivo', *Exp. Neurol.* 124:401–412.

Thoenen (1991), 'The changing scene of neurotrophic factors', *Trends. Neurosci.* 14:165–170.

Tomac et al. (1995), 'Protection and repair of the nigrostriatal dopaminergic system by GDNF in vivo', *Nature* 373:335–339.

Tresco et al. (1992), 'Polymer Encapsulated Neurotransmitter Secreting Cells', *ASAIO* 38:17–23.

Vernero et al. (1993), 'TrkA NGF receptor expression by non–cholinergic thalamic neurons', *Neuroreport* 4:959–962.

Winn et al. (1991), 'Behavioral Recovery following Intrastriatal Implantation of Microencapsulated PC12 Cells', *Exper. Neurol.* 113:322–329.

Woolf et al. (1989), 'Nerve Growth Factor Receptor is Associated With Cholinergic Neurons of the Basal Forebrain But Not the Pontomesencephalon', *Neuroscience* 30:143–152.

Yan and matheson (1995), 'In vivo neurotrophic effects of GDNF on neonatal and adult facial motor neurons', *Nature* 373:341–344.

Zurn et al. (1994), 'Glial cell–line–derived neurotrophic factor (GDNF), a new neurotrophic factor for motoneurones', *Neuroreport* 6:113–118.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 134 amino acid residues
( B ) TYPE: amino acid
( D ) TOPOLOGY: linear ( i x ) FEATURE:
( A ) NAME/KEY: inferred amino acid sequence for mature human GDNF ( x i ) SEQUENCE DESCRIPTION: SEQ ID NO:1:

```
Ser Pro Asp Lys Gln Met Ala Val Leu Pro Arg Arg Glu Arg Asn Arg
 1               5                  10                  15
Gln Ala Ala Ala Ala Asn Pro Glu Asn Ser Arg Gly Lys Gly Arg Arg
            20                  25                  30
Gly Gln Arg Gly Lys Asn Arg Gly Cys Val Leu Thr Ala Ile His Leu
        35                  40                  45
Asn Val Thr Asp Leu Gly Leu Gly Tyr Glu Thr Lys Glu Glu Leu Ile
    50                  55                  60
Phe Arg Tyr Cys Ser Gly Ser Cys Asp Ala Ala Glu Thr Thr Tyr Asp
 65                  70                  75                  80
Lys Ile Leu Lys Asn Leu Ser Arg Asn Arg Arg Leu Val Ser Asp Lys
                85                  90                  95
Val Gly Gln Ala Cys Cys Arg Pro Ile Ala Phe Asp Asp Asp Leu Ser
            100                 105                 110
Phe Leu Asp Asp Asn Leu Val Tyr His Ile Leu Arg Lys His Ser Ala
        115                 120                 125
Lys Arg Cys Gly Cys Ile
    130
```

( 2 ) INFORMATION FOR SEQ ID NO:2:

( i ) SEQUENCE CHARACTERISTICS:
( A ) LENGTH: 12 amino acid residues
( B ) TYPE: amino acid
( D ) TOPOLOGY: linear ( x i ) SEQUENCE DESCRIPTION: SEQ ID NO:2:

```
Val Phe Glu Glu Phe Ala Arg Gln Asn Leu Lys Cys
 1               5                  10
```

METHODS FOR TREATING PHOTORECEPTORS USING GLIAL CELL LINE-DERIVED NEUROTROPHIC FACTOR (GDNF) PROTEIN PRODUCT

FIELD OF INVENTION

The present invention relates generally to methods for treating injury or degeneration of retinal neurons by administering glial cell line-derived neurotrophic factor (GDNF) protein product. The invention relates specifically to methods for treating pathological conditions, such as inherited retinal degenerations and age, disease or injury-related retinopathies, in which photoreceptor degeneration occurs and is responsible for vision loss.

BACKGROUND OF THE INVENTION

Recently, several naturally occurring proteinaceous molecules have been identified based on their trophic activity on various types of neurons. These molecules are termed "neurotrophic factors". Neurotrophic factors are endogenous, soluble proteins that play a major role in neuronal survival and growth during development, as well as in the functional maintenance and plasticity of mature neurons; see Fallon and Laughlin, Neurotrophic Factors,Academic Press, San Diego, Calif. (1993). In view of their ability to promote neuron regeneration and to prevent neuron death and degeneration, it has been postulated that neurotrophic factors might be useful in treating neurodegenerative conditions of the nervous system, such as, for example, Parkinson's disease, Alzheimer's disease, amyotrophic lateral sclerosis and stroke.

Nerve damage is caused by conditions that compromise the survival and/or proper function of one or more types of nerve cells, including:

(1) physical injury, which causes the degeneration of the axonal processes (which in turn causes nerve cell death) and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine, respectively, (4) chronic metabolic diseases, such as diabetes or renal dysfunction, or (5) neurodegenerative diseases such as Parkinson's disease, Alzheimer's disease, and Amyotrophic Lateral Sclerosis, which result from the degeneration of specific neuronal populations. In order for a particular neurotrophic factor to be potentially useful in treating nerve damage, the class or classes of damaged nerve cells must be responsive to the factor; different neurotrophic factors typically affect distinctly different classes of nerve cells. It has been established that all neuron populations are not responsive to or equally affected by all neurotrophic factors.

The first neurotrophic factor to be identified was nerve growth factor (NGF). NGF is the first member of a defined family of trophic factors, called the neurotrophins, that currently includes brain-derived neurotrophic factor (BDNF), neurotrophin-3 (NT-3), NT-4/5, and NT-6 (Thoenen, Trends. Neurosci., 14:165–170, 1991; Lapchak et al., Rev. Neurosci., 3:1–10, 1993; Bothwell, Ann. Rev. Neurosci., 18:223–253, 1995). These neurotrophins are known to act through the family of trk tyrosine kinase receptors, i.e., trkA, trkB, trkC, and the low affinity p75 receptor (Lapchak et al., Rev. Neurosci., 3:1–10, 1993; Bothwell, Ann. Rev. Neurosci., 18:223–253, 1995; Chao et al., TINS, 18:321–326, 1995). In the central nervous system (CNS), the expression of trKA, the receptor for NGF, is almost exclusively limited to the cholinergic neurons in the basal forebrain (Venero et al., Neuroreport, 4:959–962, 1993), which also express p75 and trkB. These cholinergic neurons are of particular neurologic interest, because cholinergic neuronal degeneration and/or dystrophy is a hallmark of Alzheimer's disease (Hefti, J. Neurobiol., 25:1418–1435, 1994; Olson, Neurochem. Jul., 15:1–3, 1994). The basal forebrain cholinergic neurons can be readily identified in morphologic preparations using acetylcholinesterase histochemistry or with immunohistochemistry using antibody to choline acetyltransferase (ChAT), the synthetic enzyme for acetylcholine, or to p75 (Batchelor et al., J. Comp. Neurol., 284:187–204, 1989; Kiss et al., Neurosci., 27:731–748, 1988; Woolf et al., Neuroscience, 30:143–152, 1989).

Glial cell line-derived neurotrophic factor (GDNF) is a recently discovered protein identified and purified using assays based upon its efficacy in promoting the survival and stimulating the transmitter phenotype of mesencephalic dopaminergic neurons vitro (Lin et al., Science, 260:1130–1132, 1993). GDNF is a glycosylated, disulfide-bonded homodimer that is distantly related to the transforming growth factor-$\beta$ (TGF-$\beta$) superfamily of neurotrophic proteins (Krieglstein et al., EMBO J., 14:736–742, 1995; Poulsen et al., Neuron ,13:1245–1252, 1994). GDNF has been cloned, and the recombinant human GDNF (rhuGDNF) exerts trophic and survival-promoting actions on substantia nigra dopaminergic neurons and spinal cord motor neurons in vitro, as well as in vivo (Beck et al., Nature, 273:339–341, 1995; Henderson et al., Science, 266:1130–1132, 1994; Tomac et al., Nature, 273: 335–339; Yan et al., Nature, 273: 341–343; Zurn et al., Neuroreport, 6:113–118, 1994). In vivo, treatment with exogenous GDNF stimulates the dopaminergic phenotype of substantia nigra neurons and restores functional deficits induced by axotomy or dopaminergic neurotoxins in animal models of Parkinson's disease, a neurodegenerative disease characterized by the loss of dopaminergic neurons (Hudson et al., Brain Res. Bull., 36:425–432, 1995; Hoffer et al., Neurosci Lett., 182:107–111, 1994). Although originally thought to be relatively specific for dopaminergic neurons, at least in vitro, subsequent experiments have found that GDNF has neurotrophic efficacy on brain stem and spinal cord cholinergic motor neurons, both in vivo and in vitro (Oppenheim et al., Nature, 373:344–346, 1995; Zurn et al., Neuroreport, 6:113–118, 1994; Yan et al., Nature, 373: 341–344, 1995; Henderson et al., Science, 266:1062–1064, 1994). GDNF is, therefore, a factor with potential therapeutic benefit in the treatment of degenerative disorders of spinal cord motor neurons, such as amyotrophic lateral sclerosis.

Thus, evidence is beginning to emerge indicating that GDNF may have a larger spectrum of neurotrophic targets besides mesencephalic dopaminergic and somatic motor neurons (Yan and Matheson, Nature, 373:341–344, 1995; Miller et al., Soc. Neurosci. Abstr., 20:1300, 1994). GDNF messenger RNA (mRNA) has been detected in muscle and Schwann cells in the peripheral nervous system and in type I astrocytes (Schaas et al., Exp. Neurol, 124:368–371, 1993) in the central nervous system. GDNF mRNA is also expressed in high levels in the developing rat striatum (Stromberg et al., Exp. Neurol., 124:401–412, 1993), and in low levels in regions of the adult rat and human central nervous system, including striatum, hippocampus, cortex and spinal cord (Springer et al., Exp. Neurol, 127:167–170, 1994).

Of general interest to the present invention is WO93/06116 (Lin et al., Syntex-Synergen Neuroscience Joint Venture), published Apr. 1, 1993, which reports that GDNF is useful for the treatment of nerve injury, including injury associated with Parkinson's Disease. Also of interest are a report in Schmidt-Kastner et al., *Mol. Brain Res.*, 26:325–330, 1994 that GDNF mRNA became detectable and was upregulated after pilocarpine-induced seizures; reports in Schaar et al., *Exp. Neurol*, 124:368–371, 1993 and Schaar et al., *Exp. Neurol.*, 130:387–393, 1994 that basal forebrain astrocytes expressed moderate levels of GDNF mRNA under culture conditions, but that GDNF did not alter basal forebrain ChAT activity; and a report in currently pending U.S. application Ser. No. 08/535,682 filed Sep. 28, 1995 that GDNF is useful for treating injury or degeneration of basal forebrain cholinergic neurons.

In mammals, a number of ophthalmic neurodegenerative conditions or diseases involve injury or degeneration of photoreceptors. Trophic factors capable of promoting the survival or regeneration of these neurons would provide useful therapies for the treatment of such diseases.

Photoreceptors are a specialized subset of retinal neurons, that are responsible for vision. Photoreceptors consist of rods and cones which are the photosensitive cells of the retina. Each rod and cone elaborates a specialized cilium, referred to as an outer segment, that houses the phototransduction machinery. The rods contain a specific light-absorbing visual pigment, rhodopsin. There are three classes of cones in humans, characterized by the expression of distinct visual pigments: the blue cone, green cone and red cone pigments. Each type of visual pigment protein is tuned to absorb light maximally at different wavelengths. The rod rhodopsin mediates scotopic vision (in dim light), whereas the cone pigments are responsible for photopic vision (in bright light). The red, blue and green pigments also form the basis of color vision in humans. The visual pigments in rods and cones respond to light and generate an action potential in the output cells, the rod bipolar neurons, which is then relayed by the retinal ganglion neurons to produce a visual stimulus in the visual cortex.

In humans, a number of diseases of the retina involve the progressive degeneration and eventual death of photoreceptors, leading inexorably to blindness. Degeneration of photoreceptors, such as by inherited retinal dystrophies (e.g., retinitis pigmentosa), age-related macular degeneration and other maculopathies, or retinal detachment, are all characterized by the progressive atrophy and loss of function of photoreceptor outer segments. In addition, death of photoreceptors or loss of photoreceptor function results in partial deafferentation of second order retinal neurons (rod bipolar cells and horizontal cells) in patients with retinal dystrophies, thereby decreasing the overall efficiency of the propagation of the electrical signal generated by photoreceptors. Trophic factors that are capable of rescuing photoreceptors from cell death and/or restoring the function of dysfunctional (atrophic or dystrophic) photoreceptors may represent useful therapies for the treatment of such conditions.

There is some evidence that certain protein factors may promote the survival of photoreceptors. For example, photoreceptors can be rescued to some extent by basic fibroblast growth factor (bFGF) in Royal College of Surgeons (RCS) rats and in albino rats that have been damaged by exposure to constant light (Faktorovich et al., *Nature*, 347:83–86, 1990). RCS rats have an inherited mutation of a gene expressed in the retinal pigment epithelium (RPE), that results in the failure of the RPE to phagocytize the continuously shed portions of the photoreceptor outer segments and causes photoreceptor degeneration and eventually cell death.

A single injection of bFGF into the vitreous body or into the subretinal space, the extracellular space surrounding rods and cones, at the onset of the degeneration transiently rescues photoreceptors (Faktorovich et al., *Nature*, 347:83–86, 1990 ). In the light-damaged model in albino rats, bFGF injected into the subretinal space or the vitreous body two days prior to the onset of constant illumination significantly protects photoreceptors from light injury and prevents cell death (LaVail et al., *Proc. Natl. Acad. Sci. USA*, 89:11249–11253, 1992). In this model, photoreceptor survival was also seen with acidic FGF (aFGF), brain-derived neurotrophic factor (BDNF), ciliary neurotrophic factor (CNTF), and interleukin-1β (IL-1β). Moderate effects were observed with neurotrophin-3 (NT-3), insulin-like-growth factor II (IGF-II) and tumor necrosis factor-alpha (TNF-alpha). Nerve growth factor (NGF), epidermal growth factor (EGF), platelet-derived growth factor (PDGF) and IGF-I had no effect (LaVail et al., *Proc. Natl. Acad. Sci. USA*, 89:11249–11253, 1992). Also see WO 93/15608, LaVail et al.

Although bFGF is efficacious in the RCS rat and light-induced damage rat models, its therapeutic utility in humans is very limited, due to its hypotensive, mitogenic and potent angiogenic activities. In fact, bFGF injected into the vitreous body causes the invasion of blood-derived macrophages in the inner retina and can produce a massive proliferative vitreoretinopathy (Faktorovich et al., *Nature*, 347:83–86, 1990). It has also been determined, using polymerase chain reaction technology, that messenger RNA for GDNF is expressed in the eyes of postnatal day 6 and adult rats, essentially associated with the neural retina and the retinal pigment epithelium. The RPE cells produce, store and transport a variety of factors that are responsible for the survival and functional maintenance of photoreceptors. The RPE cells are also indispensable to the phototransduction process: they clear up by phagocytosis the shed tips of the outer segments of photoreceptors and recycle vitamin A. The transplantation of normal RPE cells into retinas of RCS rats prevents photoreceptor cell death (Li and Turner, *Exp. Eye Res.*, 47:911–917, 1988; Mullen and LaVail, Science, 192:799–801, 1976), suggesting the production by RPE cells of a diffusable trophic factor for photoreceptors.

There continues to exist a need for methods and therapeutic compositions useful for the treatment of photoreceptor cell injury. Such methods and therapeutic compositions would ideally protect the photoreceptors from progressive injury and promote the survival or regeneration of the damaged neuron population, without severe side effects.

SUMMARY OF THE INVENTION

The present invention provides a method for treating vision loss due to photoreceptor degeneration by administering a therapeutically effective amount of glial cell line-derived neurotrophic factor (GDNF) protein product. According to one aspect of the invention, methods are provided for treating vision loss due to photoreceptor degeneration by administering a therapeutically effective amount of GDNF protein product. It is contemplated that such GDNF protein products would include a GDNF protein such as that depicted by the amino acid sequence set forth in SEQ ID NO:1, as well as variants and derivatives thereof. The invention is based on the novel discovery that administration of GDNF protein product promotes the survival and regeneration of damaged photoreceptor neurons, which are the main population of neurons damaged in retinal degenerations leading to blindness.

GDNF protein product may be administered intraocularly at a dose between about 0.001 mg/day and 10 mg/day, preferably at a dose between about 0.01 mg/day and 1 mg/day, and most preferably at a dose between about 0.1 mg/day and 0.5 mg/day. It is also contemplated that photoreceptor degeneration or injury may be treated by the administration of a GDNF protein product in conjunction with a second therapeutic agent including, but not limited to, brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-β, and cocaine-amphetamine regulated transcript. It is also contemplated that the delivery means for the administration of a GDNF protein product in the treatment of ophthalmic conditions or diseases may advantageously involve topical formulations, ocular inserts, ocular injection, ocular implants, cell therapy or gene therapy.

The invention also provides for the use of GDNF protein product in the manufacture of a medicament or pharmaceutical composition for the treatment of injury or degeneration of photoreceptor. Such pharmaceutical compositions include topical, oral or parenteral GDNF protein product formulations. It will also be appreciated by those skilled in the art that the administration process can be accomplished via cell therapy and gene therapy means, as further described below. In yet another aspect, the present invention includes a method for providing photoreceptor cells for implantation wherein photoreceptor cells are cultured in the presence of a GDNF protein product. The invention further includes a composition which contains photoreceptor cells together with a GDNF protein product in amounts to enhance the survival and allow the continued growth and maturation of the photoreceptor cells. Numerous additional aspects and advantages of the invention will become apparent to those skilled in the art upon consideration of the following detailed description of the invention which describes presently preferred embodiments thereof.

DETAILED DESCRIPTION OF THE INVENTION

Figure 1:
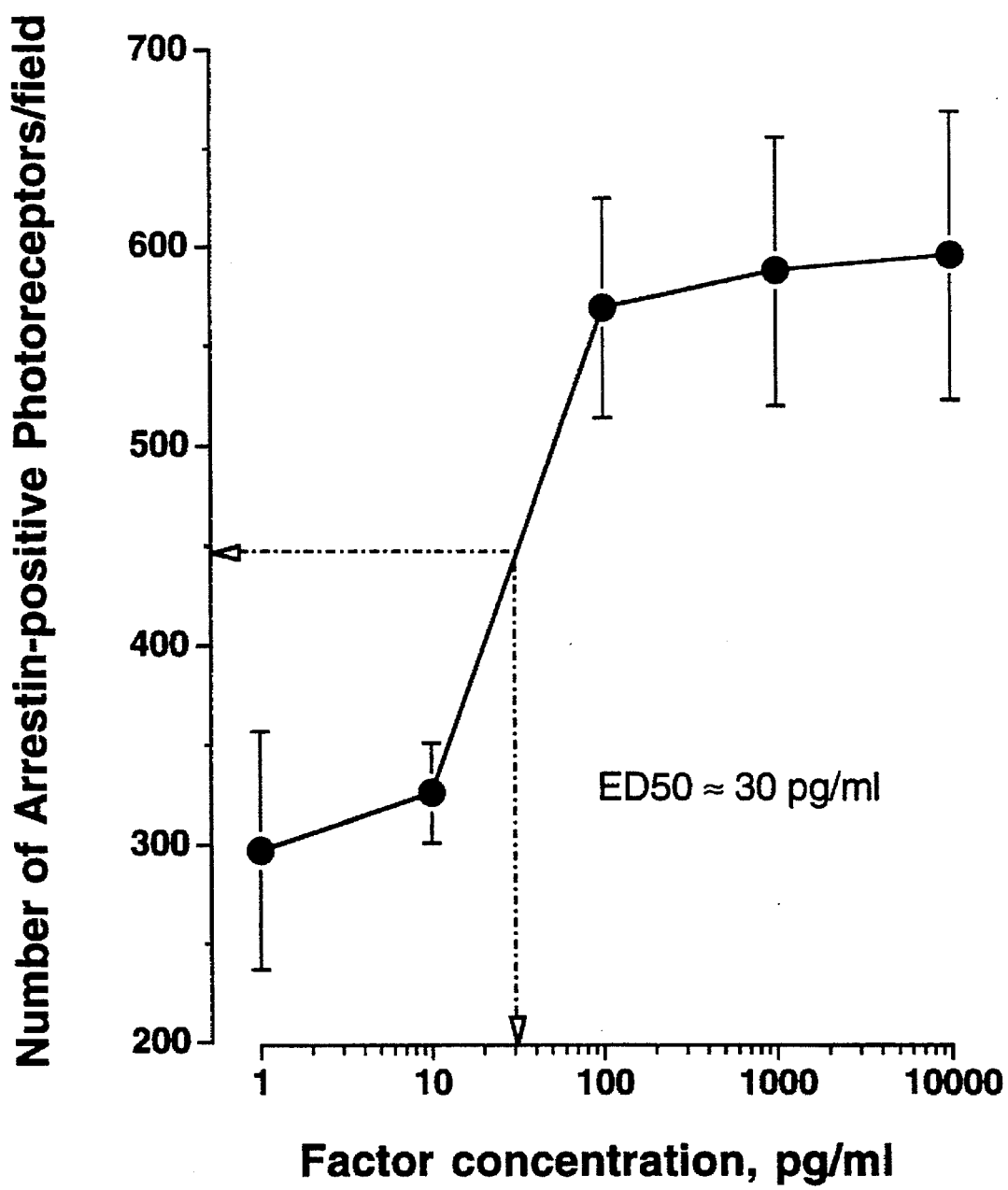
FIG. 1 depicts the effect of glial cell line-derived neurotrophic factor (GDNF) protein product on photoreceptor survival in cultures of retinal neurons. Each value is the mean±s.d. of three cultures.

The present invention is based on the demonstration that GDNF protein product has neurotrophic activity for photoreceptors. Prior to this finding, there was no suggestion or indication that GDNF might have such neurotrophic activity. The present invention provides a method for treating injury or degeneration of retinal neurons, particularly photoreceptors, by administering a therapeutically effective amount of glial cell line-derived neurotrophic factor (GDNF) protein product by means of a pharmaceutical composition, the implantation of GDNF-expressing cells, or GDNF gene therapy. The invention may be practiced using any biologically active GDNF protein product, including a GDNF having the amino acid sequence set forth in SEQ ID NO:1, variants, and derivatives thereof.

A unique cell culture technique was developed to provide the retinal neuron populations used in assessing the responsiveness of photoreceptors to GDNF protein product administration. The culture technique is described in further detail below. The treatment of these photoreceptors with a GDNF protein product revealed that in addition to promoting photoreceptor survival, the GDNF protein product also stimulated the extension of the photoreceptor's axon-like process, thereby demonstrating an effect on the morphological development of the photoreceptors. Glutamate uptake assays further demonstrated that GDNF protein product treatment enhances the functional differentiation of photoreceptors. These results indicate that among the potential benefits of GDNF protein product therapy are the promotion of photoreceptor survival, the regeneration of the photoreceptors' axons and outer segments and the restoration of visual function. Thus, the administration of a GDNF protein product would benefit conditions in which vision is lost due to the degeneration of photoreceptors, such as inherited retinal degenerations, age-related macular degeneration, injury-induced retinal degenerations, and retinal dystrophies.

The present invention further demonstrates that GDNF protein product treatment promotes photoreceptor survival in cultures of retina from mice having an inherited retinal degeneration condition. Studies of photoreceptors of rd/rd mice illustrated that GDNF protein product treatment enhanced resistance to the deleterious effect of the rd/rd mutation on photoreceptors. This indicates that GDNF protein product treatment would be useful in the in the reduction and prevention of photoreceptor degeneration and death and even in the reversal of photoreceptor degeneration in human inherited retinal diseases characterized by photoreceptor degeneration, such as, for example, retinitis pigmentosa. As illustrated by the studies described below, GDNF protein product administration may benefit a variety of pathological conditions in which photoreceptor degeneration occurs and is responsible for vision loss. These conditions include inherited retinal degenerations such as retinitis pigmentosa, Bardet-Biedl syndrome, Bassen-Kornzweig syndrome (abetalipoproteinemia), Best disease (vitelliform dystrophy), choroidemia, gyrate atrophy, congenital amaurosis, Refsum syndrome, Stargardt disease and Usher syndrome. Other retinopathies that may benefit from GDNF protein product administration include age-related macular degeneration (dry and wet forms), diabetic retinopathy, peripheral vitreoretinopathies, photic retinopathies, surgery-induced retinopathies, viral retinopathies (such as HIV retinopathy related to AIDS), ischemic retinopathies, retinal detachment and traumatic retinopathy.

According to the currently preferred embodiments of the present invention, the GDNF protein product is most advantageously administered intraocularly at a dose between about 0.001 mg/day and 10 mg/day, and preferably at a dose between about 0.01 mg/day and 1 mg/day, and most preferably at a dose between about 0.1 mg/day and 0.5 mg/day. It is further contemplated that the GDNF protein product be administered in conjunction or combination with an effective amount of a second therapeutic agent for treating retinal degeneration or retinal dystrophies. Such second therapeutic agents may include, but are not limited to: mitogens such as insulin, insulin-like growth factors, epidermal growth factor, vasoactive growth factor, pituitary adenylate cyclase activating polypeptide, interferon and somatostatin; neurotrophic factors such as brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-$\beta$, and cocaine-amphetamine regulated transcript (CART); and other growth factors such as epidermal growth factor, leukemia inhibitory factor, interleukins, interferons, and colony stimulating factors; as well as molecules and materials which are the functional equivalents to these factors.

The invention also provides for the use of GDNF protein product in preparation of a medicament for the treatment of injury or degeneration of photoreceptors, including the treatment of the diseases and conditions described above. Such GDNF protein product pharmaceutical preparations are more fully described below.

As used herein, the term "GDNF protein product" includes purified natural, synthetic or recombinant glial cell line-derived neurotrophic factor, biologically active GDNF variants (including insertion, substitution and deletion variants), and chemically modified derivatives thereof. Also included are GDNFs that are substantially homologous to the human GDNF having the amino acid sequence set forth in SEQ ID NO:1 . GDNF protein products may exist as homodimers or heterodimers in their biologically active form.

The term "biologically active" as used herein means that the GDNF protein product demonstrates similar neurotrophic properties, but not necessarily all of the same properties, and not necessarily to the same degree, as the GDNF having the amino acid sequence set forth in SEQ ID NO:1. The selection of the particular neurotrophic properties of interest depends upon the use for which the GDNF protein product is being administered.

The term "substantially homologous" as used herein means having a degree of homology to the GDNF having the amino acid sequence set forth in SEQ ID NO:1 that is preferably in excess of 70%, most preferably in excess of 80%, and even more preferably in excess of 90% or 95%. For example, the degree of homology between the rat and human protein is about 93%, and it is contemplated that preferred mammalian GDNF will have a similarly high degree of homology. The percentage of homology as described herein is calculated as the percentage of amino acid residues found in the smaller of the two sequences which align with identical amino acid residues in the sequence being compared, when four gaps in a length of 100 amino acids may be introduced to assist in that alignment, as set forth by Dayhoff, in *Atlas of Protein Sequence and Structure* v. 5, p. 124, National Biochemical Research Foundation, Washington, D.C. (1972), the disclosure of which is hereby incorporated by reference. Also included as substantially homologous is any GDNF protein product which may be isolated by virtue of cross-reactivity with antibodies to the GDNF of SEQ ID NO:1 or whose genes may be isolated through hybridization with the gene or with segments of the gene encoding the GDNF of SEQ ID NO:1.

The GDNF protein products according to the present invention may be isolated or generated by any means known to those skilled in the art. Exemplary methods for producing GDNF protein products useful in the present invention are described in U.S. patent application Ser. No. 08/182,183 filed May 23, 1994 and its parent applications; PCT Application No. PCT/US92/07888 filed Sep. 17, 1992, published as WO 93/06116 (Lin et al., Syntex-Synergen Neuroscience Joint Venture); European Patent Application No. 92921022.7, published as EP 610 254; and co-owned, co-pending U.S. application Ser. No. 08/535,681 filed Sep. 28, 1995 ("Truncated Glial Cell-Line Derived Neurotrophic Factor"), the disclosures of all of which are hereby incorporated by reference.

Naturally-occurring GDNF protein products may be isolated from mammalian neuronal cell preparations, or from a mammalian cell line secreting or expressing GDNF. For example, WO93/06116 describes the isolation of GDNF from serum-free growth conditioned medium of B49 glioblastoma cells. GDNF protein products may also be chemically synthesized by any means known to those skilled in the art. GDNF protein products are preferably produced via recombinant techniques because they are capable of achieving comparatively higher amounts of protein at greater purity. Recombinant GDNF protein product forms include glycosylated and non-glycosylated forms of the protein, and protein expressed in bacterial, mammalian or insect cell systems.

In general, recombinant techniques involve isolating the genes responsible for coding GDNF, cloning the gene in suitable vectors and cell types, modifying the gene if necessary to encode a desired variant, and expressing the gene in order to produce the GDNF protein product. Alternatively, a nucleotide sequence encoding the desired GDNF protein product may be chemically synthesized. It is contemplated that GDNF protein product may be expressed using nucleotide sequences which differ in codon usage due to the degeneracies of the genetic code or allelic variations. WO93/06116 describes the isolation and sequencing of a cDNA clone of the rat GDNF gene, and the isolation, sequencing and expression of a genomic DNA clone of the human GDNF gene. WO93/06116 also describes vectors, host cells, and culture growth conditions for the expression of GDNF protein product. Additional vectors suitable for the expression of GDNF protein product in *E. coil* are disclosed in published European Patent Application No. EP 0 423 980 ("Stem Cell Factor") published Apr. 24, 1991, the disclosure of which is hereby incorporated by reference. The DNA sequence of the gene coding for mature human GDNF and the amino acid sequence of the GDNF is shown in FIG. 19 (SEQ ID NO:5) of WO93/06116. FIG. 19 does not show the entire coding sequence for the pre-pro portion of GDNF, but the first 50 amino acids of human pre-pro GDNF are shown in FIG. 22 (SEQ ID NO:8) of WO93/06116.

Naturally-occurring GDNF is a disulfide-bonded dimer in its biologically active form. The material isolated after expression in a bacterial system is essentially biologically inactive, and exists as a monomer. Refolding is necessary to produce the biologically active disulfide-bonded dimer. Processes for the refolding and naturation of the GDNF expressed in bacterial systems are described in WO93/06116. Standard in vitro assays for the determination of GDNF activity are also described in WO93/06116 and in co-owned, co-pending U.S. application Ser. No. 08/535,681 filed Sep. 28, 1995, and are hereby incorporated by reference.

A. GDNF Variants

The term "GDNF variants" as used herein includes polypeptides in which amino acids have been deleted from ("deletion variants"), inserted into ("addition variants"), or substituted for ("substitution variants"), residues within the amino acid sequence of naturally-occurring GDNF. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made provided that the final molecule possesses GDNF biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of variants: the location of the mutation site and the nature of the mutation. In designing GDNF variants, the selection of the mutation site and nature of the mutation will depend on the GDNF characteristic(s) to be modified. The sites for mutation can be modified individually or in series, e.g., by (1) substituting first with conservative amino acid choices and then with more radical selections depending upon the results achieved, (2) deleting the target amino acid residue, or (3) inserting amino acid residues adjacent to the located site. Conservative changes in from 1 to 20 amino acids are preferred. Once the amino acid sequence of the desired GDNF protein product is determined, the nucleic acid sequence to be used in the expression of the protein is readily determined. N-terminal and C-terminal deletion variants may also be generated by proteolytic enzymes.

For GDNF deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other TGF-β superfamily members to modify the activity of GDNF. Deletions in areas of substantial homology with other TGF-β superfamily sequences will be more likely to modify the GDNF biological activity more significantly. The number of consecutive deletions will be selected so as to preserve the tertiary structure of the GDNF protein product in the affected domain, e.g., cysteine crosslinking. Non-limiting examples of deletion variants include truncated GDNF protein products lacking from one to forty N-terminal amino acids of GDNF, or variants lacking the C-terminal residue of GDNF, or combinations thereof, as described in co-owned, co-pending U.S. application Ser. No. 08/535,681 filed Sep. 28, 1995, which is hereby incorporated by reference.

For GDNF addition variants, amino acid sequence additions typically include N-and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include GDNF with an N-terminal methionyl residue (an artifact of the direct expression of GDNF in bacterial recombinant cell culture), which is designated [Met$^{-1}$]GDNF, and fusion of a heterologous N-terminal signal sequence to the N-terminus of GDNF to facilitate the secretion of mature GDNF from recombinant host cells. Such signal sequences generally will be obtained from, and thus be homologous to, the intended host cell species. Additions may also include amino acid sequences derived from the sequence of other neurotrophic factors. A preferred GDNF protein product for use according to the present invention is the recombinant human [Met$^{-1}$]GDNF.

GDNF substitution variants have at least one amino acid residue of the GDNF amino acid sequence removed and a different residue inserted in its place. Such substitution variants include allelic variants, which are characterized by naturally-occurring nucleotide sequence changes in the species population that may or may not result in an amino acid change. Examples of substitution variants (see, e.g., SEQ ID NO: 50) are disclosed in co-owned, co-pending U.S. application Ser. No. 08/535,681, filed Sep. 28, 1995, and are hereby incorporated by reference.

Specific mutations of the GDNF amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNF amino acid sequence may be modified to add glycosylation sites.

One method for identifying GDNF amino acid residues or regions for mutagenesis is called "alanine scanning mutagenesis" as described by Cunningham and Wells (*Science*, 244:1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNF variants are screened for the optimal combination of desired activity and degree of activity.

The sites of greatest interest for substitutional mutagenesis include sites where the amino acids found in GDNF proteins from various species are substantially different in terms of side-chain bulk, charge, and/or hydrophobicity. Other sites of interest are those in which particular residues of GDNF-like proteins, obtained from various species, are identical. Such positions are generally important for the biological activity of a protein. Initially, these sites are substituted in a relatively conservative manner. Such conservative substitutions are shown in Table I under the heading of preferred substitutions. If such substitutions result in a change in biological activity, then more substantial changes (exemplary substitutions) are introduced, and/or other additions or deletions may be made, and the resulting products screened for activity.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNF protein products having functional and chemical characteristics similar to those of natural GDNF. In contrast, substantial modifications in the functional and/or chemical characteristics of GDNF protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for another. Such substituted residues may be introduced into regions of the GDNF protein that are homologous with other TGF-β superfamily proteins, or into the non-homologous regions of the molecule.

B. GDNF Derivatives

Chemically modified derivatives of GDNF or GDNF variants may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight ranges from about 2 kDa to about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., *Exp. Hematol* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed GDNF, or variants thereof, linked to at least one polyethylene glycol molecule, as well as use of GDNF, or variants thereof, attached to one or more polyethylene glycol molecules via an acyl or alkyl linkage.

Pegylation may be carried out by any of the pegylation reactions known in the art. See, for example: Focus on Growth Factors, 3 (2): 4–10 (1992); EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol with the GDNF protein or variant. Any known or subsequently discovered reactive PEG molecule may be used to carry out the pegylation of GDNF protein or variant. A preferred activated PEG ester is PEG esterified to N-hydroxysuccinimide. As used herein, "acylation" is contemplated to include without limitation the following types of linkages between the therapeutic protein and a water soluble polymer such as PEG: amide, carbamate, urethane, and the like. See *Bioconjugate Chem.*, 5:133–140 (1994). Reaction conditions may be selected from any of those known in the pegylation art or those subsequently developed, but should avoid conditions of temperature, solvent, and pH that would inactivate the GDNF or variant to be modified.

Pegylation by acylation will generally result in a polypegylated GDNF protein or variant. Preferably, the connecting linkage will be an amide. Also preferably, the resulting product will be substantially only (e.g., >95%) mono-,di- or tri-pegylated. However, some species with higher degrees of peglylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNF protein or variant in the presence of a reducing agent. Pegylation by alkylation can also result in poly-pegylated GDNF protein or variant. In addition, one can manipulate the reaction conditions to favor pegylation substantially only at the a-amino group of the N-terminus of the GDNF protein or variant (i.e., a mono-pegylated protein). In either case of monopegylation or polypegylation, the PEG groups are preferably attached to the protein via a —CH2—NH— group. With particular reference to the —CH2— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNF protein (or variant) conjugate molecules (meaning GDNF protein or variant to which a polymer molecule has been attached substantially only (i.e., >95%) in a single location). More specifically, if polyethylene glycol is used, the present invention also encompasses use of pegylated GDNF protein or variant lacking possibly antigenic linking groups, and having the polyethylene glycol molecule directly coupled to the GDNF protein or variant.

Thus, it is contemplated that GDNF protein products to be used in accordance with the present invention may include pegylated GDNF protein or variants, wherein the PEG group(s) is (are) attached via acyl or alkyl groups. As discussed above, such products may be mono-pegylated or poly-pegylated (e.g., containing 2–6, and preferably 2–5, PEG groups). The PEG groups are generally attached to the protein at the α- or ε-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable condition used to react a biologically active substance with an activated polymer molecule. Methods for preparing pegylated GDNF protein or variant will generally comprise the steps of (a) reacting a GDNF protein or variant with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNF protein (or variant) conjugate molecule will generally comprise the steps of: (a) reacting a GDNF protein or variant with a reactive PEG molecule under reductive alkylation conditions, at a pH suitable to permit selective modification of the a-amino group at the amino terminus of said GDNF protein or variant; and (b) obtaining the reaction product(s).

For a substantially homogeneous population of monopolymer/GDNF protein (or variant) conjugate molecules, the reductive alkylation reaction conditions are those which permit the selective attachment of the water soluble polymer moiety to the N-terminus of GDNF protein or variant. Such reaction conditions generally provide for pKa differences between the lysine amino groups and the α-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNF protein or variant having an α-amino group at the amino terminus, and provide for a substantially homogenous preparation of monopolymer/GDNF protein (or variant) conjugate. The term "monopolymer/GDNF protein (or variant) conjugate" is used here to mean a composition comprised of a single polymer molecule attached to a molecule of GDNF protein or GDNF variant protein. The monopolymer/GDNF protein (or variant) conjugate preferably will have a polymer molecule located at the N-terminus, but not on lysine amino side groups. The preparation will preferably be greater than 90% monopolymer/GDNF protein (or variant) conjugate, and more preferably greater than 95% monopolymer/GDNF protein (or variant) conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNF Protein Product Pharmaceutical Compositions

GDNF protein product pharmaceutical compositions typically include a therapeutically effective amount of a GDNF protein product in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial CSF, possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of GDNF protein product, or for promoting the absorption or penetration of GDNF protein product across the membranes of the eye. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulations will be determined by one skilled in the art depending upon considerations such as the route of administration and desired dosage. See for example, *Remington's Pharmaceutical Sciences,* 18th Ed. (1990, Mack Publishing Co., Easton, PA 18042) pages 1435–1712, the disclosure of which is hereby incorporated by reference. Such formulations may influence the physical state, stability, rate of in vivo release, and rate of in vivo clearance of the present GDNF proteins, variants and derivatives.

Other effective administration forms, such as parenteral slow-release formulations, inhalant mists, or orally active formulations are also envisioned. For example, in a sustained release formulation, the GDNF protein product may be bound to or incorporated into particulate preparations of polymeric compounds (such as polylactic acid, polyglycolic acid, etc.) or liposomes. Hylauronic acid may also be used, and this may have the effect of promoting sustained duration in the circulation. The GDNF protein product pharmaceutical composition also may be formulated for parenteral administration, e.g., by intraocular infusion or injection, and may also include slow-release or sustained circulation formulations. Such parenterally administered therapeutic compositions are typically in the form of a pyrogen-free, parenterally acceptable aqueous solution comprising the GDNF protein product in a pharmaceutically acceptable vehicle. One preferred vehicle is sterile distilled water.

It is also contemplated that certain formulations containing GDNF protein product are to be administered orally. GDNF protein product which is administered in this fashion may be encapsulated and may be formulated with or without those carriers customarily used in the compounding of solid dosage forms. The capsule may be designed to release the active portion of the formulation at the point in the gastrointestinal tract when bioavailability is maximized and pre-systemic degradation is minimized. Additional excipients may be included to facilitate absorption of GDNF protein product. Diluents, flavorings, low melting point waxes, vegetable oils, lubricants, suspending agents, tablet disintegrating agents, and binders may also be employed.

The formulation of topical ophthalmic preparations, including ophthalmic solutions, suspensions and ointments is well known to those skilled in the art (see *Remington's Pharmaceutical Sciences,* 18th Edition, Chapter 86, pages 1581–1592 Mack Publishing Company, 1990). Other modes of administration are available, including intracameral injections (which may be made directly into the anterior chamber or directly into the vitreous chamber), subconjunctival injections and retrobulbar injections, and methods and means for producing ophthalmic preparations suitable for such modes of administration are also well known.

As used in this application, "extraocular" refers to the ocular surface and the (external) space between the eyeball and the eyelid. Examples of extraocular regions include the eyelid fornix or cul-de-sac, the conjunctival surface and the corneal surface. This location is external to all ocular tissue and an invasive procedure is not required to access this region. Examples of extraocular systems include inserts and "topically" applied drops, gels or ointments which may be used to deliver therapeutic material to these regions. Extraocular devices are generally easily removable, even by the patient.

The following patents disclose extraocular systems which are used to administer drugs to the extraocular regions. Higuchi et al. discloses in U.S. Pat. No. 3,981,303, 3,986, 510 and U.S. Pat. No. 3,995,635, a biodegradable ocular insert which contains a drug. The insert can be made in different shapes for retention in the cul-de-sac of the eyeball, the extraocular space between the eyeball and the eyelid. Several common biocompatible polymers are disclosed as suitable for use in fabricating this device. These polymers include zinc alginate, poly(lactic acid), poly(vinyl alcohol), poly(anhydrides) and poly(glycolic acid). The patents also describe membrane coated devices with reduced permeation to the drug and hollow chambers holding the drug formulation.

Theeuwes, U.S. Pat. No. 4,217,898, discloses microporous reservoirs which are used for controlled drug delivery. These devices are placed extraocularly in the ocular cul-de-sac. Among the polymer systems of interest include poly(vinylchloride)-co-poly(vinyl acetate) copolymers. Kaufman discloses in U.S. Pat. Nos. 4,865,846 and 4,882,150 an ophthalmic drug delivery system which contains at least one bio-erodible material or ointment carrier for the conjunctival sac. The patent discloses polymer systems, such as, poly(lactide), poly(glycolide), poly(vinyl alcohol) and cross linked collagen, as suitable delivery systems.

In the presently described use of GDNF protein product for the treatment of retinal disease or injury it is also advantageous that a topically applied ophthalmic formulation include an agent to promote the penetration or transport of the therapeutic agent into the eye. Such agents are known in the art. For example, Ke et al., U.S. Pat. No. 5,221,696 disclose the use of materials to enhance the penetration of ophthalmic preparations through the cornea.

Intraocular systems are those systems which are suitable for use in any tissue compartment within, between or around the tissue layers of the eye itself. These locations include subconjunctival (under the ocular mucous membrane adjacent to the eyeball), orbital (behind the eyeball), and intracameral (within the chambers of the eyeball itself). In contrast to extraocular systems, an invasive procedure consisting of injection or implantation is required to access these regions.

The following patents disclose intraocular devices. Wong, U.S. Pat. No. 4,853,224, discloses microencapsulated drugs for introduction into the chamber of the eye. Polymers which are used in this system include polyesters and polyethers. Lee, U.S. Pat. No. 4,863,457, discloses a biodegradable device which is surgically implanted intraocularly for the sustained release of therapeutic agents. The device is designed for surgical implantation under the conjunctiva (mucous membrane of the eyeball). Krezancaki, U.S. Pat. No. 4,188,373, discloses a pharmaceutical vehicle which gels at human body temperature. This vehicle is an aqueous suspension of the drug and gums or cellulose derived synthetic derivatives. Haslam et al. discloses in U.S. Pat. No. 4,474,751 and U.S. Pat. No. 4,474,752 a polymer-drug system which is liquid at room temperature and gels at body temperature. Suitable polymers used in this system include polyoxyethylene and polyoxy propylene. Davis et al. disclose in U.S. Pat. No. 5,384,333 a biodegradable injectable drug delivery polymer which provides long term drug release. The drug composition is made up of a pharmaceutically active agent in a biodegradable polymer matrix, where the polymer matrix is a solid at temperatures in the range 20° to 37° C. and is flowable at temperatures in the range 38° to 52° C. The drug delivery polymer is not limited to the delivery of soluble or liquid drug formulations. For example, the polymer can be used as a matrix for stabilizing and retaining at the site of injection drug-containing microspheres, liposomes or other particulate-bound drugs.

A particularly suitable vehicle for intraocular injection is sterile distilled water in which the GDNF protein product is formulated as a sterile, isotonic solution, properly preserved. Yet another ophthalmic preparation may involve the formulation of the GDNF protein product with an agent, such as injectable microspheres or liposomes, that provides for the slow or sustained release of the protein which may then be delivered as a depot injection. Other suitable means for the intraocular introduction of GDNF protein product includes, implantable drug delivery devices or which contain the GDNF protein product.

The ophthalmic preparations of the present invention, particularly topical preparations, may include other components, for example ophthalmically acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Sufficient tonicity enhancing agent is advantageously added so that the formulation to be instilled into the eye is hypotonic or substantially isotonic. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents include, but are not limited to, glycerin, propylene glycol and polyethylene glycol. Suitable complexing agents include caffeine, polyvinylpyrrolidone, beta -cyclodextrin or hydroxypropyl-beta -cyclodextrin. Suitable surfactants or wetting agents include, but are not limited to, sorbitan esters, polysorbates such as polysorbate 80, tromethamine, lecithin, cholesterol, tyloxapol and the like. The buffers can be conventional buffers such as borate, citrate, phosphate, bicarbonate, or Tris-HCl.

The formulation components are present in concentrations that are acceptable to the extraocular or intraocular site of administration. For example, buffers are used to maintain the composition at physiological pH or at slightly lower pH, typically within a pH range of from about 5 to about 8.

Additional formulation components may include materials which provide for the prolonged ocular residence of the extraocularly administered therapeutic agent so as to maximize the topical contact and promote absorbtion. Suitable materials include polymers or gel forming materials which provide for increased viscosity of the ophthalmic preparation. Chitosan is a particularly suitable material as an ocular release-rate controlling agent in sustained release liquid ophthalmic drug formulations (see U.S. Pat. No. 5,422,116, Yen, et. al.) The suitability of the formulations of the instant invention for controlled release (e.g., sustained and prolonged delivery) of an ophthalmic treating agent in the eye can be determined by various procedures known in the art, e.g., as described in *Journal of Controlled Release,* 6:367–373, 1987, as well as variations thereof.

Yet another ophthalmic preparation may involve an effective quantity of GDNF protein product in a mixture with non-toxic ophthalmically acceptable excipients which are suitable for the manufacture of tablets. By dissolving the tablets in sterile water, or other appropriate vehicle, ophthalmic solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc D. Administration/Delivery of GDNF Protein Product The GDNF protein product may be administered parenterally via a subcutaneous, intramuscular, intravenous, transpulmonary, transdermal, intrathecal or intracerebral route. For the treatment of ophthalmic conditions, the GDNF protein product may also be advantageously administered extraocularly or intraocularly, as described above, by topical application, inserts, injection, implants, cell therapy or gene therapy. For example, slow-releasing implants containing the neurotrophic factor embedded in a biodegradable polymer matrix can deliver GDNF protein product. GDNF protein product may be administered extracerebrally in a form that has been modified chemically or packaged so that it passes the blood-brain barrier, or it may be administered in connection with one or more agents capable of promoting penetration of GDNF protein product across the barrier. Similarly, the GDNF protein product may be administered intraocularly, or it may be administered extraocularly in connection with one or more agents capable of promoting penetration or transport of GDNF protein product across the membranes of the eye. The frequency of dosing will depend on the pharmacokinetic parameters of the GDNF protein product as formulated, and the route of administration.

The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed, especially in light of the dosage information and assays disclosed herein. Appropriate dosages may be ascertained through use of the established assays for determining dosages utilized in conjunction with appropriate dose-response data. According to the currently preferred embodiments of the present invention, the GDNF protein product is most advantageously administered intraocularly at a dose between about 0.001 mg/day and 10 mg/day, and preferably at a dose between about 0.01 mg/day and 1 mg/day, and most preferably at a dose between about 0.1 mg/day and 0.5 mg/day. It will be appreciated by those skilled in the art that the dosage used in intraocularly administered formulations will be minuscule as compared to that used in a systemic injection or oral administration.

The final dosage regimen involved in a method for treating the above-described conditions will be determined by the attending physician, considering various factors which modify the action of drugs, e.g., the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of GDNF may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence, in predictable amounts, based on a determined dosage regimen. Thus, GDNF protein products include proteins derivatized or otherwise formulated to effectuate such continuous administration.

GDNF protein product cell therapy, e.g., intraocular implantation of cells producing GDNF protein product, is also contemplated. This embodiment would involve implanting into patients cells capable of synthesizing and secreting a biologically active form of GDNF protein product. Such GDNF protein product-producing cells may be cells that are natural producers of GDNF protein product (analogous to B49 glioblastoma cells) or may be recombinant cells whose ability to produce GDNF protein product has been augmented by transformation with a gene encoding the desired GDNF protein product in a vector suitable for promoting its expression and secretion. In order to minimize a potential immunological reaction in patients being administered GDNF protein product of a foreign species, it is preferred that the natural cells producing GDNF protein product be of human origin and produce human GDNF protein product. Likewise, it is preferred that the recombinant cells producing GDNF protein product be transformed with an expression vector containing a gene encoding a human GDNF protein product. Implanted cells may be encapsulated to avoid infiltration of surrounding tissue. Human or non-human animal cells may be implanted in patients in biocompatible, semipermeable polymeric enclosures or membranes that allow release of GDNF protein product, but that prevent destruction of the cells by the patient's immune system or by other detrimental factors from the surrounding tissue. Such an implant, for example, may be attached to the sclera to produce and release GDNF protein product directly into the vitreous humor.

It is also contemplated that the patient's own cells may be transformed ex vivo to produce GDNF protein product and would be directly implanted without encapsulation. The cells would be transformed with an appropriate vector and transplanted back into the patient's retina where they would produce and release the desired GDNF protein or GDNF protein variant.

Photoreceptor cell transplantation studies designed to replace defective or lost cells due to retinal disease or damage have been performed successfully in animal models of retinal degeneration (Silverman and Hughes, *Invest. Ophthalmol. Vis. Sci.*, 30:1684–1690, 1989; Gouras et al., *Neuro-Ophthalmol.*, 10:165–176, 1990). It is contemplated that photoreceptor cells may be obtained from donor eyes and maintained in culture as described herein. The cells would then be used as a source of purified photoreceptors to be transplanted via the subretinal space into the retina of patients suffering from retinal disease or damage. These patients will be treated with immunosuppressive therapies to eliminate immunological responses and rejection of the grafted cells. The ex vivo donor retinas will be cultured in the presence of GDNF, in order to enhance their growth and survival. The patients that will receive photoreceptor cell transplants will be treated with intravitreal inneeded to promote the survival needed to promote the survival and the maturation of the grafted photoreceptors.

GDNF protein product in vivo gene therapy is also envisioned, by introducing the gene coding for GDNF protein product into targeted cells via local injection of a nucleic acid construct or other appropriate delivery vectors. (Hefti, *J. Neurobiol.*, 25:1418–1435, 1994). For example, a nucleic acid sequence encoding a GDNF protein product may be contained in an adeno-associated virus vector or adenovirus vector for delivery to the retinal cells. Alternative viral vectors include, but are not limited to, retrovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and U.S. Pat. No. 5,106,627, each of which is specifically incorporated herein by reference. A system for encapsulating living cells is described in PCT Application WO 91/10425 of Aebischer et al., specifically incorporated herein by reference. See also, PCT Application WO 91/10470 of Aebischer et al., Winn et al., *Exper. Neurol,* 113:322–329, 1991, Aebischer et al., *Exper. Neurol.,* 111:269–275, 1991; Tresco et al., ASAIO, 38:17–23, 1992, each of which is specifically incorporated herein by reference. Additional implantable devices are described in WO 93/21902 (International Application No. PCT/US93/03850) which is incorporated herein by reference. Techniques for formulating a variety of other sustained- or controlled-delivery means, such as liposome carriers, bio-erodible particles or beads and depot injections, are also known to those skilled in the art.

It should be noted that the GDNF protein product formulations described herein may be used for veterinary as well as human applications and that the term "patient" should not be construed in a limiting manner. In the case of veterinary applications, the dosage ranges should be the same as specified above.

Other aspects and advantages of the present invention will be understood upon consideration of the following illustrative examples. The examples address the effect of GDNF protein product on both normal and mutated retinal neurons. In addition, the examples set forth unique techniques for culturing retinal cells.

EXAMPLES

MATERIALS AND METHODS

The materials used in the following Examples were obtained as follows.

Cell Culture Media

High glucose Dulbecco's Modified Eagle's Medium (DMEM; #11965–092), Ham's F12 medium (F12; #11765–021), Leibovitz's L15 medium without sodium bicarbonate (#41300–039); B27 medium supplement (#17504–010), penicillin/streptomycin (#15070–014), L-glutamine (#25030–016), Dulbecco's phosphate-buffered saline (D-PBS; #14190–052), Hank's balanced salt solution with calcium and magnesium salts (HBSS; #24020–026), N-2-hydroxyethylpiperazine-N'-2-ethanesulfonic acid (HEPES; #15630–015), mouse laminin (#23017–015), bovine serum albumin and fractionV (#110–18–017) were all from GIBCO/BRL, Grand Island, N.Y. Heat-inactivated horse serum was from HyClone, Logan, Utah. Poly-L-ornithine hydrobromide (P-3655), bovine insulin (I-5500), human transferrin (T-2252), putrescine (P-6024), progesterone (P-6149) and sodium selenite (S-9133) were all from Sigma Chemical Company, Saint-Louis, Mo. Papain, deoxyribonuclease I (DNAase) and ovalbumin (Papain dissociation system) were from Worthington Biochemicals, Freehold, N.J. Falcon sterile 96-well microplates (#3072), tissue culture plastic ware and polypropylene centrifuge tubes were from Beckton-Dickinson, Oxnard, Calif. Nunc Lab-Tek tissue culture chamber coverglasses (#136439) were from Baxter, Irvine, Calif. Nitex 20 µm nylon mesh (#460) was from Tetko, Elmsford, N.Y. The 4" dissecting forceps and 4" dissecting scissors were from Roboz Surgical, Washington, D.C.

Antibodies, Radioisotopes and Related Reagents

Polyclonal rabbit antibody and mouse monoclonal rho4D2 anti-bovine rhodopsin antibodies were from the University of British Columbia, Vancouver, Canada. The polyclonal rabbit antibody was directed to the following synthetic peptide sequence of the rod-specific protein arrestin: Val-Phe-Glu-Glu-Phe-Ala-Arg-Gln-Asn-Leu-Lys-Cys (SEQ ID NO:2). Biotinylated horse anti-mouse IgG, biotinylated goat anti-rabbit IgG, peroxidase-conjugated avidin/biotin complex and Texas Red-conjugated streptavidin (ABC Elite; kit PK-6100) were from Vector Laboratories, Burlingame, Calif. Fluorescein isothiocyanate conjugated rabbit anti-mouse immunoglobulins were from Dako Corporation (Carpinteria, Calif.). 3', 3'-diaminobenzidine was from Cappel Laboratories, West Chester, Pa. Superblock blocking buffer in PBS (#37515) was from Pierce, Rockford, Ill. Triton X-100 (X100), Nonidet P-40 (N6507) and hydrogen peroxide (30%, v/v; H1009) were from Sigma. L-[3, $4^3$H]-Glutamic acid (NET-490; 40–80 Ci/mmol) was from New England Nuclear, Boston, Mass. Optiphase Supermix scintillation cocktail was from Wallac, Turku, Finland. White ViewPlate-96 microplates (#6005182) were from Packard Instruments Corporation, Meriden, Conn. All other reagents were obtained from Sigma Chemical Company (Saint-Louis, Mo.), unless otherwise specified.

Preparation of Media

A basal medium was prepared as a 1:1 mixture of DMEM and F12 medium, and was supplemented with B27 medium supplement added as a 50-fold concentrated stock solution. The B27 medium supplement consists of biotin, L-carnitine, corticosterone, ethanolamine, D(+)-galactose, reduced glutathione, linoleic acid, linolenic acid, progesterone, putrescine, retinyl acetate, selenium, T3 (triodo-1-thyronine, DL-alpha-tocopherol (vitamin E), DL-alpha-tocopherol acetate, bovine serum albumin, catalase, insulin, superoxide dismutase and transferrin. L-glutamine was added at a final concentration of about 2 mM, penicillin at about 100 IU/l, and streptomycin at about 100 mg/l. Heat-inactivated horse serum was added to a final concentration of about 2.5 percent, D-glucose was added to a final concentration of about 5 g/l, HEPES buffering agent was added to a final concentration of about 20 mM, bovine insulin was added to a final concentration of about 2.5 mg/ml, and human transferrin was added to a final concentration of about 0.1 mg/ml. After mixing, the pH was adjusted to about 7.3 and the medium was kept at 4° C. The media were prepared fresh just before use in order to minimize inter-experimental variations. Plastic pipettes and containers were used throughout to minimize protein adsorption.

GDNF Protein Product Solutions

Purified human recombinant GDNF protein products were prepared as 1 mg/ml solutions in D-PBS (phosphate buffered saline prepared with distilled water) containing five percent bovine serum albumin. The solutions were stored at −85° C. in aliquots. Serial dilutions were prepared in 96-well microplates. Ten microliters of ten-fold concentrated GDNF protein product solutions were added to cell cultures containing culture medium (90 µl). Control cultures received D-PBS with 5 percent albumin (10 µl). The GDNF protein product treatments were initiated one hour after cells were seeded and, in some instances, repeated every other day.

Culture Substratum

To encourage optimal attachment of photoreceptors on substratum, outer segment outgrowth and neurite outgrowth, the microtiter plate surfaces (the culture substratum) were modified by sequential coating with poly-L-ornithine followed by laminin in accordance with the following procedure. The plate surfaces were completely covered with a 0.1 mg/ml sterile solution of polyornithine in 0.1M boric acid (pH 8.4 ) for at least one hour at room temperature, followed by a sterile wash with Super-Q water. The water wash was then aspirated and a 1 µg/ml solution of mouse laminin in PBS was added and incubated at 37° C. for two hours. These procedures were conducted just before using the plates in order to ensure reproducibility of the results.

Preparation of Chick and Mouse Photoreceptor Cultures

Seventeen-day-old White Leghorn chick embryos and 5-day-old C57Bl/6 mouse pups (obtained from Jackson Laboratories, Bar Harbor, Me.) were killed by decapitation and the eyes were dissected sterilely into L15 medium (without sodium bicarbonate). A maximum of 24 eyes were processed per experiment. The eyes were hemisected, and the lens and vitreous were removed. The neural retinas were carefully removed and dissected free of the pigment epithelium, cut into small (about 1 square mm or less) fragments and placed into ice-cold D-PBS. The cells were collected, and then transferred into 10 ml dissociation medium (120 units papain and 2000 units DNAase in HBSS). The cells were incubated for 45 minutes at about 37° C. on a rotary platform shaker at about 200 rpm. The cells were then dispersed by trituration through fire-polished Pasteur pipettes, sieved through a 20 µm Nitex nylon mesh to discard undissociated tissue, and centrifuged for five minutes at 200×g using an IEC clinical centrifuge. The resulting cell pellet was resuspended into HBSS containing ovalbumin and about 500 units DNAase, layered on top of a 4 percent ovalbumin solution (in HBSS) and centrifuged for about 10 minutes at 500×g. The final pellet was resuspended in complete culture medium (see above), adjusted to about 15,000 cells/ml, and seeded in 90 µl aliquots into the 6 mm-wells of 96-well microplates previously coated with polyornithine and laminin. Attachment of cells occurred rapidly, and the plating efficiency was about 75 percent.

Cultures of photoreceptors from adult mouse retina

Cultures of adult photoreceptors were obtained by seeding dissociated retinal cells from post-natal day 18 to 39 mice on top of pre-established monolayers of post-natal day 5 mouse retinal glial cells or rat retina pigment epithelium cells. Dissociation procedures and culture media were the same as described above. Cultures of retinal glial cells and pigment epithelium cells were established in tissue culture flasks (225 cm$^2$ Costar flasks) and grown until confluence was reached. The cells were then detached by a short (about two minute) incubation with 0.1% trypsin and plated in 96-well microplates or 16-well glass coverslip chambers. Dissociated adult retinal cells were added after about 3 to 5 days.

Cultures of photoreceptors from rd/rd mouse retina

Rd/rd C57Bl/6 mice (obtained from Jackson Laboratories, Bar Harbor, Me.) have an inherited photoreceptor degeneration resulting from the expression of a mutation in the beta subunit of phosphodiesterase (an enzyme localized in the outer segments and involved in the phototransduction processes). These mice provide a useful model to study the role of trophic factors on lesioned photoreceptors. Photoreceptor death in rd/rd mice peaks at around 10 days after birth. Cultures of rd/rd photoreceptors were established from 5-day-old mice and maintained in cultures for eight days, covering the period of maximal photoreceptor death. The dissociated retinal cells were seeded on top of a pre-established monolayer of retinal glial cells (see above) at a density of about 10,000 cells per 6-mm well and were maintained in the culture medium described above.

Immunohistochemistry of Photoreceptors

To characterize mouse photoreceptors, an indirect immunoperoxidase method described by Louis et al. (*J. Pharmacol. Exp. Therap.*, 262:1274–1283, 1992; *Science*, 259:689–692, 1993) was used, with slight modifications as follows. Cultures of photoreceptors were fixed for about 30 minutes at room temperature with 4 percent paraformaldehyde in D-PBS, pH 7.4, followed by three washes in D-PBS (200 µl per 6-mm well). The fixed cultures were then incubated in Superblock blocking buffer in PBS, containing one percent Nonidet P-40 to increase the penetration of the antibodies. The anti-rhodopsin antibodies (rabbit and mouse) were then applied at a dilution of between 1:1000–1:4000 in the same buffer, and the cultures were incubated for one hour at 37° C. on a rotary shaker. After three washes with D-PBS, the photoreceptor-bound antibodies were detected using goat-anti-rabbit or horse-anti-mouse anti-mouse biotinylated IgG (Vectastain kit from Vector Laboratories, Burlingame, Calif.) at about a 1:500 dilution: these secondary antibodies were incubated with the cells for about one hour at 37° C., the cells were then washed three times with D-PBS. The secondary antibodies were then labeled with an avidin-biotin-peroxidase complex diluted at 1:500, and the cells were incubated for about 45 minutes at 37° C. After three more washes with D-PBS, the labeled cell cultures were reacted for 5–20 minutes in a solution of 0.1M Tris-HCl, pH 7.4, containing 0.04% 3',3'-diaminobenzidine-(HCl)4, 0.06 percent $NiCl_2$ and 0.02 percent hydrogen peroxide.

For double staining experiments, the cultures were grown on glass coverslip chambers. After paraformaldehyde fixation, permeabilization and blocking of the non-specific sites (as described above), the cultures were incubated with rabbit anti-arrestin and mouse anti-rhodopsin antibodies. Arrestin was revealed by further incubation with biotinylated goat anti-rabbit IgG, followed by Texas-Red conjugated streptavidin (1:200 dilution). Rhodopsin was revealed by further incubation with fluorescein isothiocyanate-conjugated rabbit anti-mouse IgG. Fluorescence was visualized under epifluorescence, using the appropriate filter combinations for Texas Red and fluorescein.

Determining PhotoreCeptor Survival

Mouse photoreceptor cultures were fixed, processed and immunostained as described above, and the photoreceptor cultures were then examined with bright-light optics at 200×magnification. The number of stained neurons was counted in one diametrical 1×6 mm strip, representing about 20 percent of the total surface area of a 6 mm-well. Viable photoreceptors were characterized as having a regularly-shaped cell body, with a usually short axon-like process. Photoreceptors showing signs of degeneration, such as having irregular, vacuolated perikarya or fragmented neurites, were excluded from the counts (most of the degenerating photoreceptors, however, detached from the culture substratum). Cell numbers were expressed either as cells/6-mm well or as the fold-change relative to control cell density.

Neurite Analysis

Morphometric analysis of neurite (i.e., the process at the photoreceptor cell body) development was performed using 6-day-old cultures of mouse retina. Cultures containing about 10,000 neurons per 6-mm well were immunostained for arrestin and examined with brightfield optics. Photographs of randomly chosen fields of photoreceptors in control and treated 6-mm well cultures were taken with an Optronics video-camera and enlarged to a final magnification of approximately 800-fold. Neuritic size was determined by measuring the length of the neurites of each photoreceptor with a stylus coupled to a SummaSketchII digitizing tablet (Summagraphics Corporation, Houston, Tex.), utilizing a digitizing program (MacMeasure 1.9) and a Macintosh Centris 650 personal computer.

RESULTS

Example 1

Promotion of rod photoreceptor survival and development in cultures of post-natal mouse retina.

Cultures of mouse retinas were used to demonstrate the effect of GDNF protein product on photoreceptor survival. The photoreceptor cultures were established by seeding dissociated retinal cells into polyornithine-laminin-coated microplates at a density of about 12,500 per 6-mm well in DMEM/F12 supplemented with B27 medium supplement, 2.5% heat-inactivated horse serum, D-glucose, HEPES, insulin and transferrin. Photoreceptors were identified by the presence of arrestin (a rod-specific antigen) and rhodopsin (the rod-specific visual pigment) immunoreactivities.

After 6 days in vitro the cells were fixed with 4% paraformaldehyde, and photoreceptors in the cultures were immunostained using arrestin, a marker that identifies mammalian rod photoreceptors. After immunostaining, as described above, phase-contrast micrography of a field selected for the presence of different retinal cell types revealed photoreceptors (identifiable as small cells covered by a brown reaction material after immunostaining for arrestin), neurons and Mueller glial cells. Bright-field examination of a defined field demonstrated that the anti-arrestin antiserum, raised in rabbit against an arrestin-specific synthetic peptide, exclusively bound to rod photoreceptors and did not bind to other retinal neurons, or Mueller glial cells.

Based on arrestin-immunoreactivity, it was determined that about 90 percent of the cells in the cultures were photoreceptors. The remaining cells were large multipolar and smaller unipolar NSE-positive neurons. The cells were then immunostained for rhodopsin. About 50% of the photoreceptors expressed the rod visual pigment rhodopsin, as determined by immunostaining with the mouse monoclonal anti-rhodopsin antibody. Photoreceptors appeared as rounded cells with a small cell body diameter, one or two neurites and, in some cases, a short vertical process that represents the connecting cilium. At this level of resolution, there was no evidence of outer segment formation.

Post-natal day 6 mouse retina cultures were then evaluated for the effect of GDNF protein product administration on photoreceptor survival. Cultures of photoreceptors (10,000/6-mm well) were treated with human recombinant GDNF protein product (ten-fold serial dilutions ranging from 10 ng/ml to 1 pg/ml). The cultures were fixed after six days and immunostained for arrestin. Photoreceptor survival was determined by counting the number of arrestin-positive cells per 6 sq. mm fields (representing about 21% of the total surface area of a 6-mm well).

In cultures that were not treated with GDNF protein product, the number of photoreceptors declined steadily over time to reach about 25 percent of the initial number after six days in culture. Treatment of the cultures with *E. coli* expressed recombinant human GDNF protein product resulted in an about two-fold increase in the number of viable arrestin-positive photoreceptors after six days in culture (See FIG. 1; each value is the mean±s.d. of three cultures.) The effect of GDNF protein product was maximal at about 200 pg/ml, with an ED50 of about 30 pg/ml.

Figure 2:
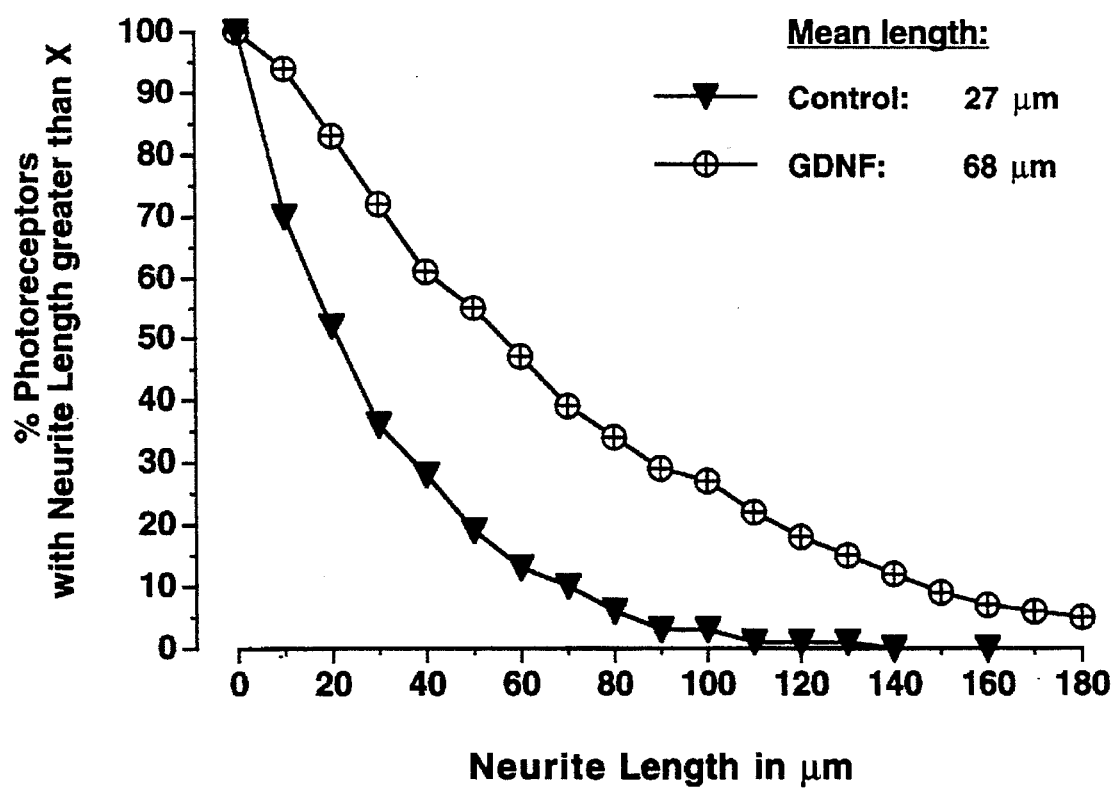
FIG. 2 depicts the promotion of photoreceptor neurite outgrowth by GDNF protein product. The data are expressed as a cumulative frequency distribution plot of the neurite lengths. The percentage of photoreceptors (ordinate) with neurites longer than a given length in micrometers (abscissa) is plotted.

In addition to promoting photoreceptor survival, the addition of the GDNF protein product also stimulated the extension of their axon-like process (further referred to as neurite), thereby demonstrating an effect on the morphological development of the photoreceptors. Cultures of photoreceptors were incubated for six days with or without recombinant human GDNF protein product (1 ng/ml). The cultures were then immunostained for arrestin. About 715 photoreceptors from two independent control cultures and 710 photoreceptors from two independent GDNF protein product-treated cultures were photographed and analyzed for neurite lengths. The effect of GDN F protein product administration on neurite outgrowth was quantified by measuring neurite lengths of the photoreceptors. FIG. 2 depicts the promotion of photoreceptor neurite outgrowth by GDNF protein product. The data are expressed as a cumulative frequency distribution plot of the neurite lengths. The percentage of photoreceptors (ordinate) with neurites longer than a given length in micrometers (abscissa) is plotted. The addition of GDNF protein product shifted the distribution of neurite lengths to higher values compared with untreated cultures. Some photoreceptors in the GDNF protein product-treated cultures displayed neurites about 180 μm in length, whereas the longest neurites observed in untreated cultures were 100 μm in length. The mean neurite length of photoreceptors in GDNF protein product-treated cultures was 68 μm, compared to 27 μm in control cultures.

Photoreceptors utilize glutamate as their neurotransmitter to signal to second order neurons. In cultures consisting of >90% photoreceptors, the degree of glutamate uptake by the cells indicates the number and activity of high-affinity glutamate reuptake transporter sites present on photoreceptors and thereby reflects their functional differentiation. The stimulation of glutamate uptake by GDNF protein product administration was evaluated to assess its effects on photoreceptor functional differentiation. Cultures were grown as described above and were either untreated or treated with recombinant human GDNF protein product for six days. Cultures were then processed for [$^3$H]-glutamate uptake (50 nM; 1.5 million dpm/ml; one hour incubation at 37° C.) in accordance with the following procedure.

Glutamate Uptake Assay: Glutamate uptake was determined in cultures of photoreceptors from 5-day-old mouse pups that had been established in 96-well microplates. The cultures were washed with about 100 μl of pre-warmed uptake buffer which consists of a modified Krebs-Ringer solution, pH 7.4 containing about 120 mM NaCl, 4,7 mM KCl, 1.8 mM CaCl2, 1.2 mM MgSO4, 32 mM NaHPO4, 1.3 mM EDTA, and 5.6 mM D-glucose. The cells were then preincubated at 37° C for about 10 minutes in uptake buffer. Tritiated L-glutamate (about 60 Ci/mmol) was then added to the cultures at a concentration of about 50 nM in 75 μl of uptake buffer and the cultures were incubated for about 60 minutes at 37° C. The uptake was arrested by aspiration of the incubation medium followed by three rapid washes with about 120 μl of ice-cold uptake buffer. The cells were then lysed by addition of 200 ILl of Optiphase Supermix scintillation cocktail (Wallac), and radioactivity was determined by scintillation spectrometry using a Wallac MicrobetaPlus 96-well microplate counter. The results are expressed either as dpm/6-mm well or as the fold-change change relative to control cultures.

Figure 3:
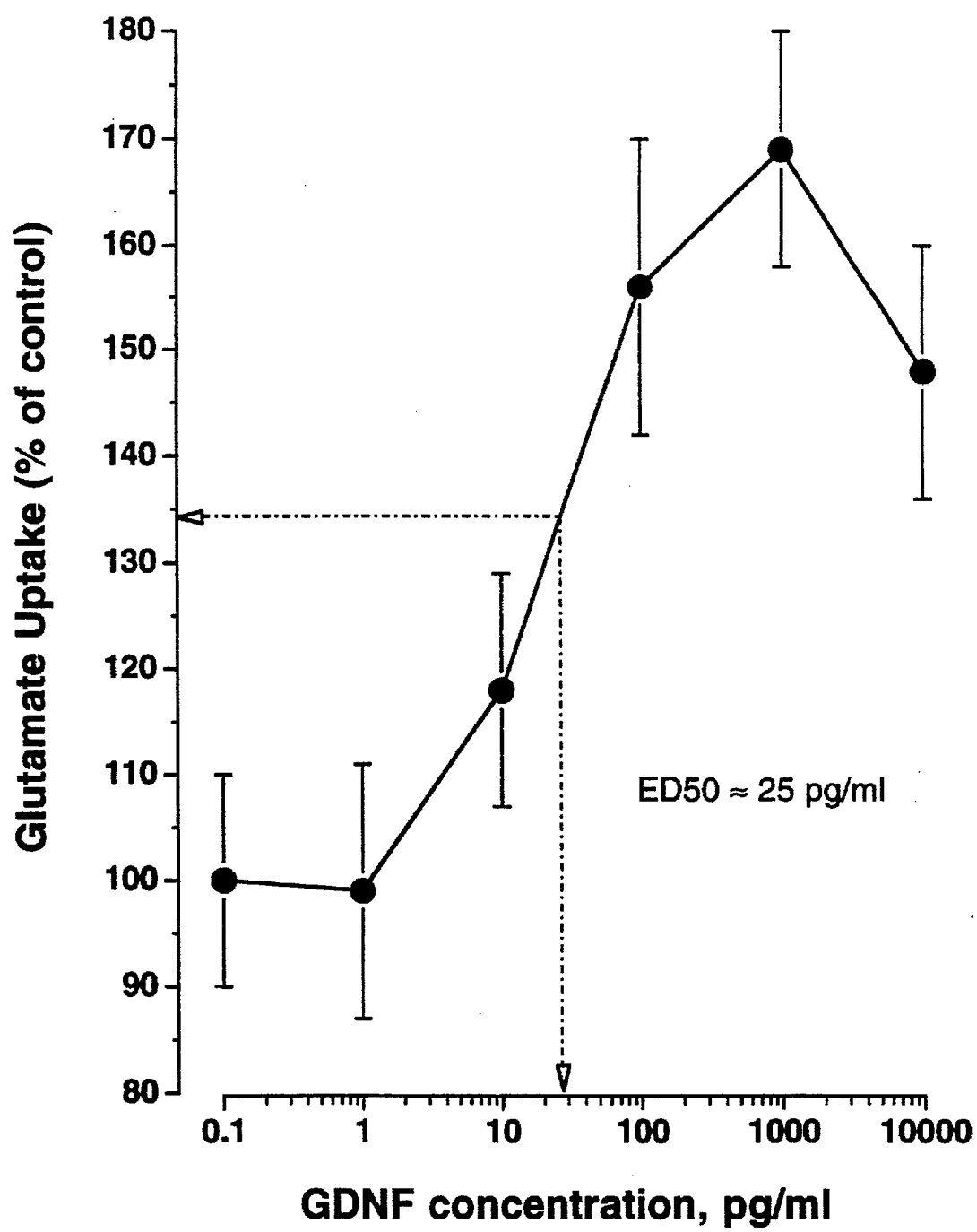
FIG. 3 depicts the stimulation of glutamate uptake by GDNF protein product in cultures of photoreceptors. The results are expressed as the percentages of the glutamate uptake values (in dpm/well) found in control cultures. Each data point is the mean±s.d. of 3 wells from a representative experiment.

The GDNF protein product was found to stimulate glutamate uptake in a dose-dependent fashion, with maximal activity reached at about 200 pg/ml and an ED50 of about 25 pg/ml. The results are illustrated in FIG. 3. Each data point is the mean±s.d. of 3 wells from a representative experiment. Similar results were obtained in two independent experiments. The results demonstrate that in addition to promoting the survival and morphological development of photoreceptors, GDNF enhances the maturation of neurotransmission-related functions, such as glutamate uptake, that are critical to the visual transduction process.

Example 2

Promotion of rod photoreceptor survival and regeneration in cultures of adult mouse retina.

Photoreceptor development is complete at about three weeks after birth. By this time, photoreceptors have developed functional outer segments that concentrate the cellular machinery necessary for phototransduction, including the visual pigments. Mature rat photoreceptors were dissociated from 18- and 39-day old retinas and maintained in culture for over a week. The neurons were seeded (at a density of about 2,500/6-mm well ) on top of a pre-existing monolayer of retinal glial cells. Glial cells encourage adhesion of dissociated photoreceptors and provide them with nutrients and factors essential for their development. Adult photoreceptors co-cultured with retinal glial cells were identified by double-immunostaining for arrestin and rhodopsin using the antibodies and immunostaining techniques described above.

Figure 4:
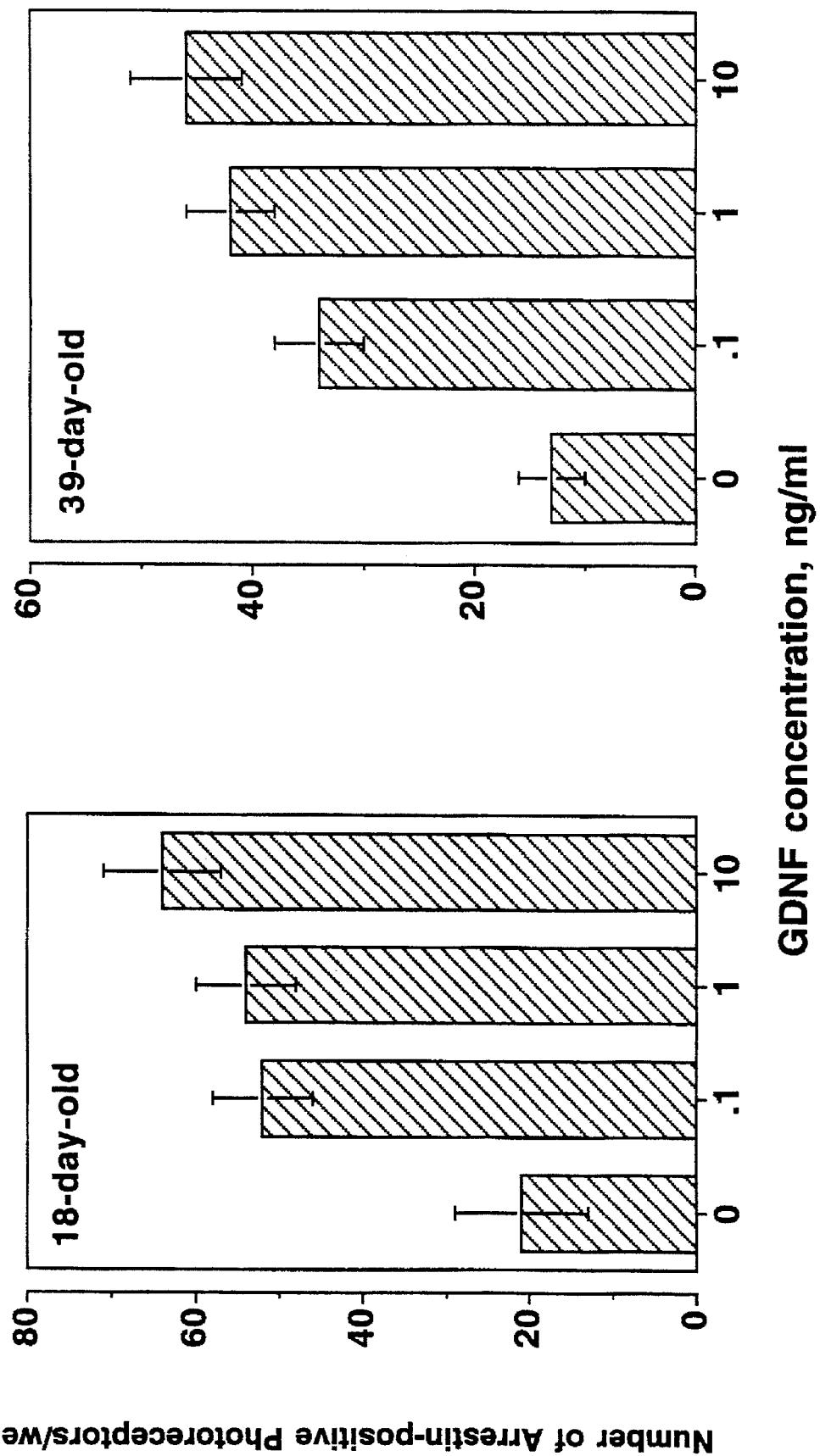
FIG. 4 depicts the promotion of photoreceptor survival by GDNF protein product in cultures of retinal neurons. Changes in photoreceptor number in response to GDNF protein product treatment in cultures from 18-day-old and 39-day-old mice are depicted. Each value is the mean±s.d. of 2–3 cultures.

Cultures were treated with recombinant human GDNF protein product (0.1, 1 or 10 ng/ml). The cells were fixed after seven days and immunostained for arrestin. Photoreceptor survival was determined by counting the number of arrestin-positive neurons per 6-mm well. The number of rod photoreceptors in cultures of both 18- and 39-day old retinas was about 3.5-fold higher in cultures treated with GDNF protein product (see FIG. 4; each value is the mean±s.d. of 2–3 cultures). Maximal support was found with GDNF protein product concentrations of about 300 pg/ml, with an ED50 of about 40 pg/ml. These results illustrate the changes in photoreceptor number, and thus, the promotion of photoreceptor survival in response to treatment with GDNF protein product.

In a further study, dissociated retina cells were seeded on top of a pre-established monolayer of mouse retina glial cells (1000 retina cells/6-mm well) and treated with recombinant human GDNF protein product (1 or 10 ng/ml). The cultures were fixed after seven days and immunostained for arrestin. In addition to promoting photoreceptor survival, it was found that GDNF protein product strongly enhanced morphological development of the photoreceptors as demonstrated by the outgrowth of their axonal processes and, in some instances, the outgrowth of a short apical process reminiscent of an immature outer segment. These cultures originated from adult retinas in which the photoreceptors were fully developed. Since the photoreceptors lost their processes during the dissociation procedure, the current data demonstrate the ability of GDNF protein product to promote the regeneration of photoreceptors, and in particular promote the development of their axonal processes and outer segments which are critical to the visual process. These results indicate that the administration of a GDNF protein product may be a useful therapy for conditions in which vision is lost due to the degeneration of photoreceptors, such as senile macular degeneration, inherited retinal degenerations and other retinal dystrophies.

Example 3

Promotion of rod photoreceptor survival in cultures of retina from mice with inherited retinal degeneration (rd/rd).

Rd/rd mice carry a mutation in the beta-subunit of phosphodiesterase (an enzyme localized in the outer segments and involved in the phototransduction processes), which results in its malfunction and causes early-onset photoreceptor degeneration and the fulminant death of photoreceptors. Mutations similar to rd/rd are found in humans and are responsible for a subset of retinitis pigmentosa cases. Photoreceptor death in rd/rd mice peaks at around 10 days after birth. These mutant mice provide a useful model for studying the effects of GDNF protein product on the survival of rd/rd photoreceptors.

Cultures of rd/rd photoreceptors were established from 5-day-old mice and maintained in cultures for seven days, a period covering the occurrence of maximal photoreceptor death. Due to their inherent vulnerability, the dissociated rd/rd photoreceptors were seeded (at a density of about 2,500/6-mm well) on top of a pre-established monolayer of retinal glial cells (as described above). Cultures of rd/rd retinas were compared to cultures of cells from normal (wild-type) mice retinas obtained from animals of the same age and processed in the same way. Cultures were treated with recombinant human GDNF protein product (1 ng/ml), fixed after seven days and immunostained for arrestin. Photoreceptor survival was determined by counting the number of arrestin-positive neurons per 6-mm well.

Figure 5:
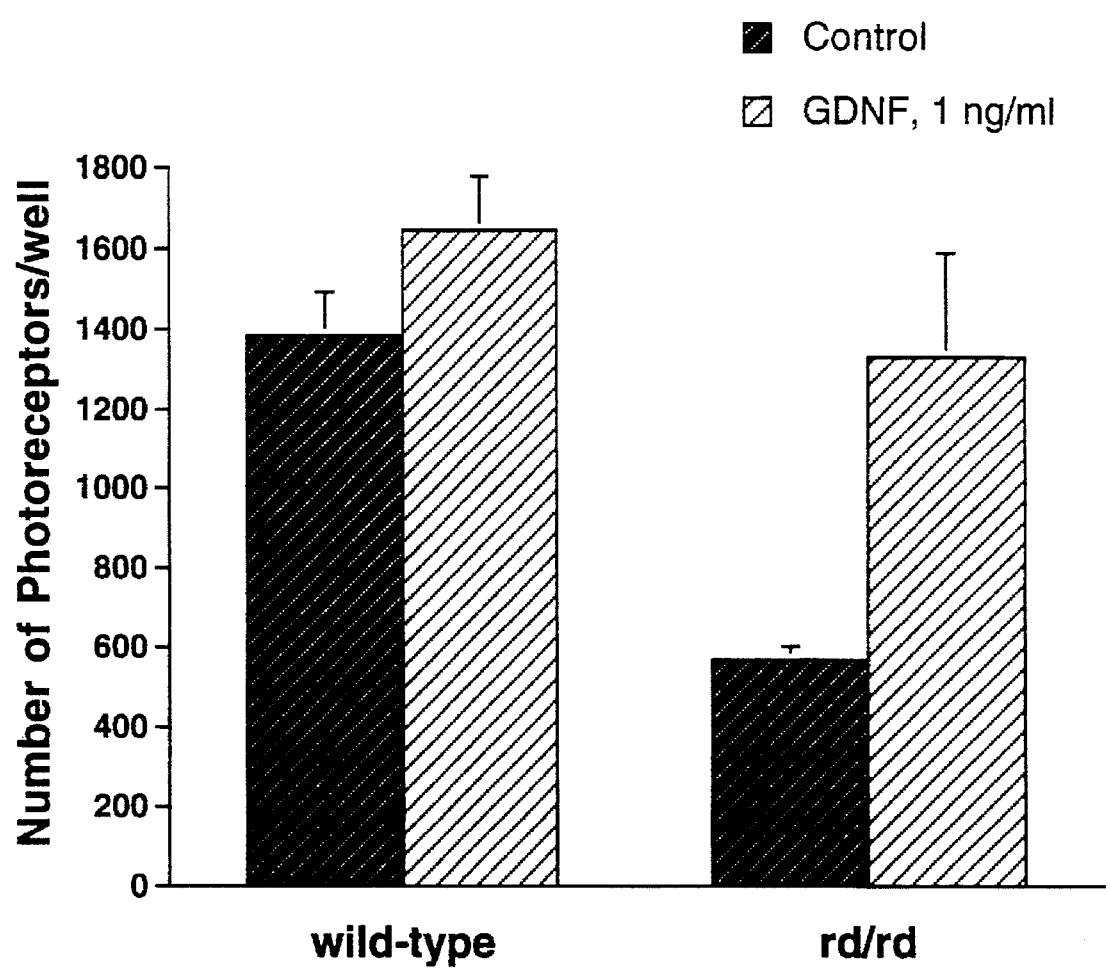
FIG. 5 depicts the promotion of photoreceptor survival by GDNF protein product in cultures of rd/rd mouse retinas. Photoreceptor survival was determined by counting the number of arrestin-positive neurons per 6-mm well. Each value is the mean±s.d. of 3–4 cultures.

The addition of GDNF protein product caused a modest (about 15%) but significant increase in photoreceptor number after seven days culture in vitro (see FIG. 5; each value is the mean-±s.d. of 3–4 cultures). In contrast, and in spite of the glial cells support, when GDNF protein product was not added the number of photoreceptors in cultures of rd/rd mice dropped sharply to reach about 40% of wild-type photoreceptors after seven days. In the presence of GDNF protein product (1 ng/ml), the number of surviving rd/rd photoreceptors was increased by about 2.5-fold, reaching the survival levels seen in cultures of untreated wild-type photoreceptors. These data demonstrate that GDNF protein product treatment made the mutant photoreceptors more resistant to the stress imposed upon them by the rd/rd mutation. This indicates that the administration of GDNF protein product may be useful for the treatment of inherited retinal degenerations, such as retinitis pigmentosa.

Example 4

Promotion of cone photoreceptor survival and outer segment development in cultures of embryonic chick retina.

The development of the chick visual system is much more precocious than in rodents. Photoreceptor outer segment outgrowth starts at about 11–12 days of agestational age, and at birth the photoreceptors are fully developed. Therefore, the effect of GDNF protein product administration on photoreceptor survival and regeneration can be studied in cultures of embryonic chick retinas.

Cultures of embryonic day 17 chick retina cells were grown in 96-well microplates, as described above, and fixed with 4% paraformaldehyde after six days in vitro. The cultures were found to contain about 60 percent photoreceptor cells and 40 percent large multipolar neurons. Phase-contrast micrographs of a representative field of the control cultures revealed the two major types of retinal cells present in the culture: cone photoreceptors, identifiable by the presence of a lipid droplet in the apical part of the cell soma, and retinal neurons. The photoreceptor cells were identified by oval cell bodies that were occupied almost exclusively by the nucleus, a short inner segment with a small lipid droplet, a single shod, unbranched neurite emerging from a point opposite to the lipid droplet, and a short distal cilium. These features are characteristic of cones. Anti-rhodopsin immunostaining was performed, as described above, and bright-field micrography of a 6-day-old culture revealed the presence of rod photoreceptorso It was determined that about 20% of the photoreceptors were rods. The remaining 80% of that do not contain rhodoone photoreceptors, that do not contain rhodopsin.

Figure 6:
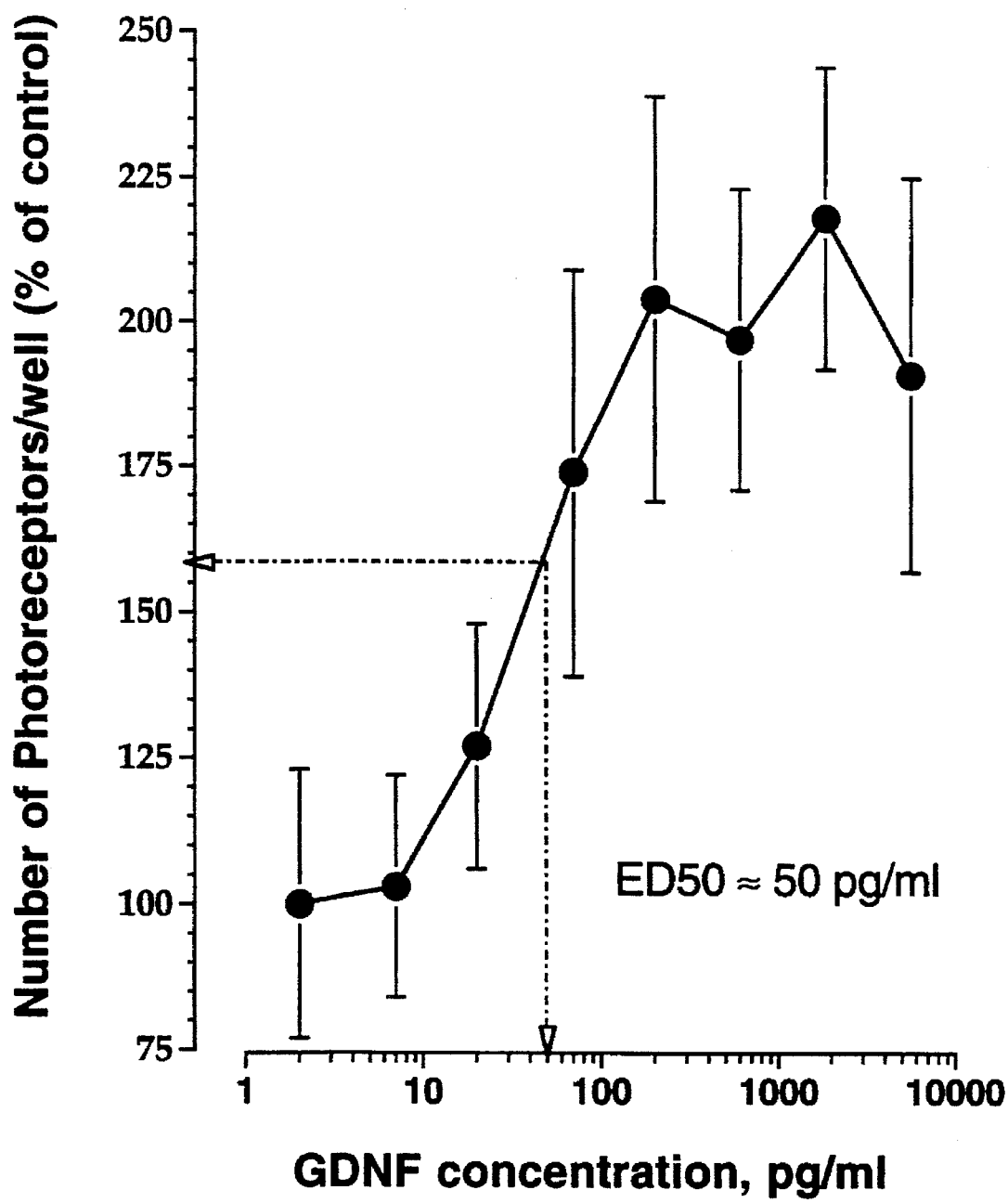
FIG. 6 depicts the effect of GDNF on photoreceptor survival in cultures of chick retina. Photoreceptor survival was determined by counting the number of cones per 6 sq. mm diametrical strips (representing about 21% of the total area of a 6-mm well). Each value is the mean±s.d. of 3 cultures.

FIG. 6 depicts the effect of GDNF protein product on photoreceptor survival in cultures of embryonic day 17 chick retina. Cultures of dissociated retina cells (plated at a density of about 10.000/6-mm well) were treated with recombinant human GDNF protein product (ten-fold serial dilutions ranging from 10 ng/ml to 1 pg/ml). The cultures were fixed after six days with 4% paraformaldehyde and observed under phase-contrast optics. Cone photoreceptors were identified by the presence of a phase-bright lipid droplet. The lipid droplet marks the junction between the inner and outer segments. Photoreceptor survival was determined by counting the number of cones per 6 sq. mm diametrical strips (representing about 21% of the total area of a 6-mm well). Each value is the mean±s.d. of 3 cultures. The number of cones found in the chick retina cultures was about two-fold higher in the GDNF protein product-treated cultures than in untreated cultures. The maximal GDNF protein product effect was observed at about 200 pg/ml, with an ED50 of about 50 pg/ml.

Photoreceptor cell morphology was evaluated by phase-contrast micrography, and GDNF protein product was found to promote the development of both the inner segments and outer segments and of the axonal process. In contrast to untreated cultures, cultures treated with GDNF protein product (1 ng/ml for seven days) contained a large proportion of cone photoreceptors which appeared as highly elongated, polarized, compartmentalized cells. These cones had an elongated inner segment that was in some cases connected to a tri-dimensional, phase-bright structure characteristic of an outer segment. Other cones developed a thick, long and branched neurite. In some instances, double cones extending two outer segments (typical of avian retinas) were observed in GDNF protein product-treated cultures. In addition to the cell survival/proliferation effects, the effect of GDNF protein product administration on outer segment development in the chick cultures demonstrates its ability to promote the regeneration of outer segments damaged by the dissociation procedure. This in turn indicates that GDNF protein product administration would also useful in the treatment of retinal dystrophies, in addition to inherited retinal degenerative conditions and retinopathies.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. A method for treating injury or degeneration of photoreceptors, comprising administering to a subject suffering from such photoreceptor injury or degeneration a therapeutically effective amount of a glial cell line-derived neurotrophic factor (GDNF) protein product.

2. The method of claim 1 wherein the injury or degeneration of the photoreceptors is associated with retinitis pigmentosa, Bardet-Biedl syndrome, Bassen-Kornzweig syndrome (abetalipoproteinemia), Best disease (vitelliform dystrophy), choroidemia, gyrate atrophy, congenital amaurosis, Refsum syndrome, Stargardt disease and Usher syndrome, age-related macular degeneration, diabetic retinopathy, peripheral vitreoretinopathies, photic retinopathies, surgery-induced retinopathies, vital retinopathies, ischemic retinopathies, retinal detachment or traumatic retinopathy.

3. The method of claim 1 wherein the GDNF protein product comprises the amino acid sequence set forth in SEQ ID NO:1 or a variant, or a derivative thereof.

4. The method of claim 3 wherein the GDNF protein product has the amino acid sequence set forth in SEQ ID NO:1.

5. The method of claim 3 wherein the GDNF protein product is [Met$^{-1}$]GDNF.

6. The method of claim 1 wherein the GDNF protein product comprises GDNF attached to a water soluble polymer.

7. The method of claim 6 wherein the water soluble polymer is polyethylene glycol.

8. The method of claim 1 wherein the GDNF protein product comprises a truncated GDNF protein product.

9. The method of claim 1 wherein the GDNF protein product is administered at a dose between about 0.001 mg/day and 10 mg/day.

10. The method of claim 9 wherein the GDNF protein product is administered at a dose between about 0.1 mg/day and 0.5 mg/day.

11. The method of claim 1 wherein the GDNF protein product is administered as a sustained-release pharmaceutical composition.

12. The method of claim 1 wherein the GDNF protein product is administered as a topical, oral or parenteral pharmaceutical composition.

13. The method of claim 1 wherein the GDNF protein product is administered by cell therapy or gene therapy means wherein cells have been modified to produce and secrete the GDNF protein product.

14. The method of claim 13 wherein the cells have been modified ex vivo.

15. The method of claim 13 wherein the cells have been modified in vivo.

16. The method of claim 1 further comprising administering to the patient an effective amount of a second therapeutic agent for treating retinal disease.

17. The method of claim 16 wherein the second therapeutic agent is selected from the group consisting of brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-$\beta$, and cocaine-amphetamine regulated transcript.

18. The method of claim 1 wherein the GDNF protein product is administered by a delivery means selected from the group consisting of ocular inserts, ocular injection or ocular implants.

19. A method for providing photoreceptor cells for implantation comprising culturing dissociated photoreceptor cells in the presence of a glial cell line-derived neurotrophic factor (GDNF) protein product.

* * * * *

UNITED STATES PATENT AND TRADEMARK OFFICE
CERTIFICATE OF CORRECTION

PATENT NO. : 5,641,750

DATED : June 24, 1997

INVENTOR(S) : Jean-Claude Louis

It is certified that error appears in the above-indentified patent and that said Letters Patent is hereby corrected as shown below:

Page 2, column 2, line 3, change "*Inc.*" to --*Int.*--.

line 42, change "matheson" to --Matheson--.

Column 2, line 8, change "*Jul.*, 15" to --*Int.*, 25--.

line 21, change "vitro" to --in vitro--.

line 31, change "273" to --373--.

line 32, change "1130-1132" to --1062-1064-- and "273: 335-339;" to --373: 335-339, 1995;--.

line 33, change "273: 341-343," to --373: 341-344, 1995--.

line 59, change "Schaas" to --Schaar--.

Column 11, line 50, change "lie" to --Ile--.

Column 15, line 3, change "alkyiation" to --alkylation--.

Column 23, line 42, change "(triodo-1-thyronine," to --(triodo-1-thyronine),--.

Column 25, line 28, delete "anti-mouse".

line 52, change "PhotoreCeptor" to --Photoreceptor--.

Column 27, line 22, change "GDN F" to --GDNF--.

line 57, change "4,7" to --4.7--.

line 67, change "IL1" to --µl--.

Column 28, line 4, delete "change".

UNITED STATES PATENT AND TRADEMARK OFFICE
CERTIFICATE OF CORRECTION

PATENT NO. : 5,641,750

DATED : June 24, 1997

INVENTOR(S) : Jean-Claude Louis

It is certified that error appears in the above-indentified patent and that said Letters Patent is hereby corrected as shown below:

Column 30, line 13, change "shod" to --short--.

line 18, change "photoreceptorso" to --photoreceptors.--.

line 20, change "that do not contain rhodoone" to --the photoreceptors were cone--.

line 60, change "also useful" to --also be useful--.

Signed and Sealed this

Twenty-first Day of October 1997

BRUCE LEHMAN

*Attest:*

*Attesting Officer*    *Commissioner of Patents and Trademarks*